(12) United States Patent
Forsyth et al.

(10) Patent No.: US 12,076,070 B2
(45) Date of Patent: Sep. 3, 2024

(54) TIME MULTIPLEXED WAVEFORM FOR SELECTIVE CELL ABLATION

(71) Applicant: BOSTON SCIENTIFIC SCIMED, INC., Maple Grove, MN (US)

(72) Inventors: Bruce R. Forsyth, Hanover, MN (US); Larry D. Canady, Jr., Ham Lake, MN (US); Jonathan Tyler Gorzycki, Blaine, MN (US); Timothy A Ostroot, Cokato, MN (US); Hong Cao, Maple Grove, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 572 days.

(21) Appl. No.: 16/818,014

(22) Filed: Mar. 13, 2020

(65) Prior Publication Data
US 2020/0289827 A1    Sep. 17, 2020

Related U.S. Application Data

(60) Provisional application No. 62/819,120, filed on Mar. 15, 2019.

(51) Int. Cl.
*A61B 18/12*    (2006.01)
*A61B 18/00*    (2006.01)

(52) U.S. Cl.
CPC .......... *A61B 18/1206* (2013.01); *A61B 18/12* (2013.01); *A61B 2018/00577* (2013.01); *A61B 2018/00613* (2013.01); *A61B 2018/1246* (2013.01)

(58) Field of Classification Search
None
See application file for complete search history.

(56) References Cited

U.S. PATENT DOCUMENTS

| | | |
|---|---|---|
| 5,019,034 A | 5/1991 | Weaver et al. |
| 5,370,675 A | 12/1994 | Edwards et al. |
| 5,718,246 A | 2/1998 | Vona |
| 5,855,576 A | 1/1999 | Leveen et al. |

(Continued)

FOREIGN PATENT DOCUMENTS

| | | |
|---|---|---|
| JP | H11346436 A | 12/1999 |
| JP | 2019500170 A | 1/2019 |

(Continued)

OTHER PUBLICATIONS

StarBurst XL RFA Electrodes, Angiodynamics Inc. 2013. 2 pages.

(Continued)

*Primary Examiner* — Sean W Collins
*Assistant Examiner* — Nora W Rhodes
(74) *Attorney, Agent, or Firm* — Seager, Tufte & Wickhem LLP

(57) ABSTRACT

Methods and devices for performing ablation using time multiplexed waveforms are disclosed. The increased efficacy of monophasic waveforms is combined with the reduced side effects of biphasic waveforms by distributing components of the waveform across over a broader time interval than that typically used in a conventional biphasic waveform. Charge balancing occurs upon completion of therapy delivery within a time period that avoids muscle stimulation, while allowing unbalanced waveforms to be delivered during stimulation.

10 Claims, 13 Drawing Sheets

(56) References Cited

U.S. PATENT DOCUMENTS

| | | | |
|---|---|---|---|
| 5,863,290 | A | 1/1999 | Gough et al. |
| 6,010,613 | A | 1/2000 | Walters et al. |
| 6,041,252 | A | 3/2000 | Walker et al. |
| 6,043,066 | A | 3/2000 | Mangano et al. |
| 6,278,895 | B1 | 8/2001 | Bernard |
| 6,326,177 | B1 | 12/2001 | Schoenbach et al. |
| 6,387,671 | B1 | 5/2002 | Rubinsky et al. |
| 6,428,534 | B1 | 8/2002 | Joye et al. |
| 6,638,277 | B2 | 10/2003 | Schaefer et al. |
| 6,714,816 | B1 | 3/2004 | Heller et al. |
| 6,912,471 | B2 | 6/2005 | Heigl et al. |
| 6,994,706 | B2 | 2/2006 | Chornenky et al. |
| 7,245,963 | B2 | 7/2007 | Draghia-Akli et al. |
| 7,306,595 | B2 | 12/2007 | Ostrovsky et al. |
| 7,306,940 | B2 | 12/2007 | Miklavcic et al. |
| 7,416,549 | B2 | 8/2008 | Young et al. |
| 7,456,012 | B2 | 11/2008 | Ryttsn et al. |
| 7,794,458 | B2 | 9/2010 | Mcintyre et al. |
| 7,799,022 | B2 | 9/2010 | Fernald et al. |
| 7,850,681 | B2 | 12/2010 | Lafontaine |
| 8,014,854 | B2 | 9/2011 | Schroeppel et al. |
| 8,048,067 | B2 | 11/2011 | Davalos et al. |
| 8,114,070 | B2 | 2/2012 | Rubinsky et al. |
| 8,152,801 | B2 | 4/2012 | Goldberg et al. |
| 8,211,104 | B2 | 7/2012 | Mccullagh et al. |
| 8,251,986 | B2 | 8/2012 | Chornenky et al. |
| 8,282,631 | B2 | 10/2012 | Davalos et al. |
| 8,465,484 | B2 | 6/2013 | Davalos et al. |
| 8,540,710 | B2 | 9/2013 | Johnson et al. |
| 8,603,087 | B2 | 12/2013 | Rubinsky et al. |
| 8,647,338 | B2 | 2/2014 | Chornenky et al. |
| 8,801,709 | B2 | 8/2014 | Prakash et al. |
| 8,915,911 | B2 | 12/2014 | Azure |
| 8,920,416 | B2 | 12/2014 | Pham et al. |
| 8,926,606 | B2 | 1/2015 | Davalos et al. |
| 9,005,189 | B2 | 4/2015 | Davalos et al. |
| 9,168,096 | B2 | 10/2015 | Kreindel |
| 10,105,172 | B2 | 10/2018 | Johnson et al. |
| 10,154,869 | B2 | 12/2018 | Onik et al. |
| 11,045,648 | B2 | 6/2021 | Dewitt et al. |
| 2001/0044596 | A1 | 11/2001 | Jaafar |
| 2002/0107515 | A1 | 8/2002 | Edwards et al. |
| 2002/0115991 | A1 | 8/2002 | Edwards |
| 2003/0009110 | A1 | 1/2003 | Tu et al. |
| 2004/0186468 | A1 | 9/2004 | Edwards |
| 2004/0267333 | A1* | 12/2004 | Kronberg ............ A61N 1/36021 607/72 |
| 2005/0267467 | A1 | 12/2005 | Paul et al. |
| 2006/0142801 | A1 | 6/2006 | Demarais et al. |
| 2006/0293730 | A1 | 12/2006 | Rubinsky et al. |
| 2007/0025919 | A1 | 2/2007 | Deem et al. |
| 2008/0275445 | A1 | 11/2008 | Kelly et al. |
| 2009/0247933 | A1 | 10/2009 | Maor et al. |
| 2009/0254148 | A1 | 10/2009 | Borgens et al. |
| 2009/0281477 | A1* | 11/2009 | Mikus ................ A61B 18/1477 606/41 |
| 2009/0326638 | A1 | 12/2009 | Atanasoka et al. |
| 2010/0023004 | A1* | 1/2010 | Francischelli ..... A61B 18/1492 606/41 |
| 2010/0261994 | A1 | 10/2010 | Davalos et al. |
| 2011/0238057 | A1 | 9/2011 | Moss et al. |
| 2012/0053403 | A1 | 3/2012 | Ducharme et al. |
| 2012/0197356 | A1 | 8/2012 | Wei et al. |
| 2012/0220999 | A1* | 8/2012 | Long ................ A61B 18/1477 606/41 |
| 2012/0310230 | A1 | 12/2012 | Willis |
| 2012/0330299 | A1 | 12/2012 | Webster et al. |
| 2013/0184702 | A1 | 7/2013 | Neal, II et al. |
| 2014/0121663 | A1 | 5/2014 | Pearson et al. |
| 2014/0128859 | A1 | 5/2014 | Lee |
| 2014/0128936 | A1 | 5/2014 | Laufer et al. |
| 2016/0038749 | A1* | 2/2016 | Maile ................ A61N 1/37252 607/31 |
| 2016/0113709 | A1 | 4/2016 | Maor |
| 2016/0199661 | A1 | 7/2016 | Willard et al. |
| 2017/0035499 | A1 | 2/2017 | Stewart |
| 2017/0105793 | A1 | 4/2017 | Cao et al. |
| 2017/0245928 | A1 | 8/2017 | Xiao et al. |
| 2018/0250508 | A1* | 9/2018 | Howard ............ A61B 18/1206 |
| 2018/0272124 | A1 | 9/2018 | Kibler et al. |
| 2018/0303543 | A1 | 10/2018 | Stewart et al. |
| 2019/0143106 | A1 | 5/2019 | Dewitt et al. |
| 2019/0223943 | A1 | 7/2019 | Forsyth et al. |
| 2020/0069366 | A1* | 3/2020 | Clark ................ A61B 18/1492 |
| 2020/0129230 | A1 | 4/2020 | Forsyth et al. |
| 2020/0138506 | A1* | 5/2020 | Fraasch ............ A61B 18/1233 |
| 2020/0155227 | A1 | 5/2020 | Cao et al. |
| 2020/0289185 | A1 | 9/2020 | Forsyth et al. |
| 2020/0289188 | A1 | 9/2020 | Forsyth et al. |
| 2020/0289827 | A1 | 9/2020 | Forsyth et al. |

FOREIGN PATENT DOCUMENTS

| | | | |
|---|---|---|---|
| WO | 2015021113 | A1 | 2/2015 |
| WO | 2017119934 | A1 | 7/2017 |
| WO | 2018200800 | A1 | 11/2018 |
| WO | WO-2019133606 | A1 * | 7/2019 ......... A61B 18/1206 |

OTHER PUBLICATIONS

StarBurst Talon Fusion RFA Electrodes, Angiodynamics Inc. 2013. 2 pages.

Deodhar et al; "Irreversible Electroporation Near the Heart: Ventricular Arrhythmias Can Be Prevented With ECG Synchronization." AJR 196:W330-W335, Mar. 2011. Accessed on Jul. 16, 2019.

Beebe et al; "Nanosecond Pulsed Electric Field (nsPEF) Effects on Cells and Tissues: Apoptosis Induction and Tumor Growth Inhibition", IEEE Transactions on Plasma Science, 6 pages, Mar. 2002.

Kennedy et al; "Cationic Peptide Exposure Enhances Pulsed-Electric-Field-Mediated Membrane Disruption", PLOS One, vol. 9, Issue 3, 17 pp. Mar. 2014.

Miklavcic et al; "The Importance of Electric Field Distribution for Effective in Vivo Electroporation of Tissues", Biophysical Journal, vol. 74, pp. 2152-2158, May 1998.

Distelmaier et al; "Midterm Safety and Efficacy of Irreversible Electroporation of Malignant Tumors Located Close to Major Portal or Hepatic Veins", Radiology, vol. 285, No. 3, 1023-1031, Dec. 2017.

Rubinsky et al; "Irreversible Electroporation: A New Ablation Modality—Clinical Implications." Technology in Cancer Research and Treatment, vol. 6, No. 1, pp. 37-48, Feb. 2007.

Swartz et al; "Sparking New Frontiers: Using in Vivo Electroporation for Genetic Manipulations", Developmental Biology, 233, pp. 13-21, 2001.

Tsong, "Electroporation of Cell Membranes," Biophysical Journal, vol. 60, pp. 297-306, Aug. 2, 1991.

International Search Report and Written Opinion dated Jul. 2, 2020 for International Application No. PCT/US2020/022582.

International Search Report and Written Opinion Dated Jul. 7, 2020 for International Application No. PCT/US2020/022571.

International Search Report and Written Opinion dated Jun. 26, 2020 for International Application No. PCT/US2020/022578.

* cited by examiner

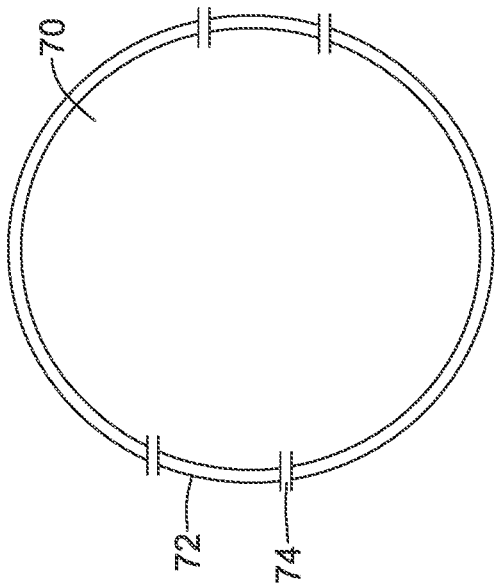
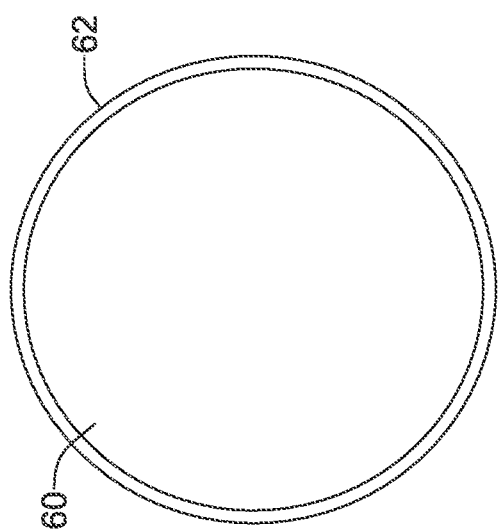
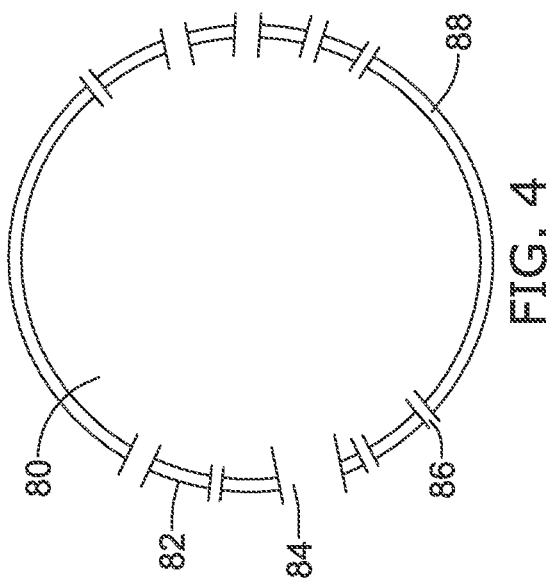

TIME MULTIPLEXED WAVEFORM FOR SELECTIVE CELL ABLATION

CROSS-REFERENCE TO RELATED PATENT DOCUMENTS

The present application claims the benefit of and priority to U.S. Provisional Patent Application 62/819,120, filed Mar. 15, 2019, titled TIME MULTIPLEXED WAVEFORM FOR SELECTIVE CELL ABLATION, the disclosure of which is incorporated herein by reference. The present application is also related to U.S. Provisional Patent Application 62/819,135, filed Mar. 15, 2019, and titled SPATIALLY MULTIPLEXED WAVEFORM FOR SELECTIVE CELL ABLATION, and U.S. Provisional Patent Application 62/819,101, filed Mar. 15, 2019, and titled WAVEFORM GENERATOR AND CONTROL FOR SELECTIVE CELL ABLATION, the disclosures of which are incorporated herein by reference.

BACKGROUND

Removal or destruction of diseased tissue is a goal of many cancer treatment methods. Tumors may be surgically removed, however, less invasive approaches garner much attention. Tissue ablation is a minimally invasive method of destroying undesirable tissue in the body. Ablation may be thermal or non-thermal.

Thermal ablation either adds or removes heat to destroy undesirable cells. For example, cryoablation kills cells by freezing of the extracellular compartment resulting in cell dehydration beginning at −15 C with membrane rupture occurring at colder temperatures. Cryoablation is known to (beneficially) stimulate an antitumor immune response in the patient.

Heat-based thermal ablation adds heat to destroy tissue. Radio-frequency (RF) thermal, microwave and high intensity focused ultrasound ablation can each be used to raise localized tissue temperatures well above the body's normal 37 degrees C. For example, RF thermal ablation uses a high frequency electric field to induce vibrations in the cell membrane that are converted to heat by friction. Cell death occurs in as little as 30 seconds once the cell temperature reaches 50 degrees C., while at higher temperatures cell death is instantaneous. Heat based ablation, however, may not prompt the desirable immune response associated with cryoablation.

Thermal ablation techniques using heat or cold each suffer from the drawback that they have little or no ability to spare normal structures in the treatment zone. Collateral injury to vascular, neural and other structures is undesirable. For this reason, various researchers have explored non-thermal ablation as well.

Non-thermal ablation techniques include electro-chemotherapy and irreversible electroporation. Electroporation refers to a phenomenon in which the plasma membrane of a cell exposed to high voltage pulsed electric fields becomes temporarily permeable due to destabilization of the lipid bilayer. Pores then form, at least temporarily. Electro-chemotherapy combines pore formation with the introduction of chemicals that cause cell death. Because the chemical molecules used are large, only cells subject to the electric fields will absorb the chemical material and subsequently die, making for useful selectivity in the treatment zone. Irreversible electroporation (IRE) omits the chemicals, and instead uses the electric fields, usually with increased amplitude, to expand pores in the cell membrane beyond the point of recovery, causing cell death for want of a patent cell membrane. The spatial characteristics of the applied field control which cells and tissue will be affected, allowing for better selectivity in the treatment zone than with thermal techniques.

One challenge with the electrical (whether thermal or not) ablation techniques is that of local muscle stimulation. A monophasic waveform is thought to provide better results for IRE in terms of causing certain cell death. However, monophasic waveforms tend to cause muscle stimulation, requiring the use of a paralytic to facilitate surgery, among other problems. A biphasic waveform avoids the muscle stimulation, but may not be as effective at the same energy level and/or amplitude as the monophasic waveform. Simply raising power to make the biphasic waveform more effective runs the risk of causing thermal ablation. Enhancements and alternatives to the state of the art are desired to allow a waveform to be used that is as effective as monophasic stimulus for IRE, while avoiding muscle stimulation and thus obtaining the benefits of both monophasic and biphasic therapy.

OVERVIEW

The present inventors have recognized, among other things, that a problem to be solved is the provision of ablation therapy that combines high efficacy and tissue selectivity while avoiding muscle stimulation. A number of examples shown below use a time multiplexing of therapy outputs to achieve such aims.

A first illustrative and non-limiting example takes the form of a signal generator adapted for use in delivery of tissue ablation energy comprising a therapy output block including to a voltage conversion circuit, an energy storage circuit and an output control circuit; an input/output circuit adapted to couple to a probe for delivery of tissue ablation energy, the input/output circuit defining a plurality of output channels such that a probe coupled thereto and having a plurality of electrodes can be used with separate activation of subsets of the plurality of electrodes; a user interface allowing a user to control the signal generator and adapted to display one or more parameters of tissue ablation energy to be delivered by the signal generator; a controller coupled to the therapy output block and the user interface; a memory coupled to the controller and having stored instructions for the delivery of a treatment cycle, the treatment cycle comprising: a first output of a first polarity at a first amplitude and having a first pulse width as a first phase; a second output of a second polarity, opposite the first polarity, at a second amplitude and having a second pulse width, the second pulse width being less than half the first pulse width; and a third output using the second polarity at a third amplitude less than the second amplitude, the third pulse width being greater than the second pulse width; wherein the sum of the first, second and third outputs yields a balanced charge to limit muscle stimulation associated with the multiphasic ablation waveform.

Additionally or alternatively to the first illustrative example, the stored instructions may define the first and second amplitudes to exceed an irreversible electroporation threshold, and the third amplitude to be less than an irreversible electroporation threshold.

Additionally or alternatively to the first illustrative example, the stored instructions may define at least one of the first and second amplitudes to exceed an irreversible electroporation threshold, and the third amplitude to be less than a reversible electroporation threshold.

Additionally or alternatively to the first illustrative example, the stored instructions may define the first, second and third pulse widths such that one of the first, second and third time periods exceeds the sum of the other two of the first, second and third time periods.

Additionally or alternatively to the first illustrative example, the stored instructions may define the first pulse width in the range of about 1 to 50 microseconds, and the second pulse width in the range of about 0.5 to 10 microseconds.

Additionally or alternatively to the first illustrative example, the stored instructions may define the first, second and third pulse widths as summing to a duration of less than one millisecond.

Additionally or alternatively to the first illustrative example, the signal generator may further comprise monitoring circuitry coupled to the input/output circuitry to monitor at least one of current or voltage in at least one therapy output channel, and the stored instructions may define a plurality of iterations in which: in a first iteration, the first, second and third outputs are generated while the control circuitry monitors one or more of impedance of current flow for each of the first, second and third outputs; in second iteration, the first, second and third outputs are again generated, except that at least one of the amplitude or pulse width of at least one of the first, second and third outputs is adjusted to reduce change imbalance, if any, resulting from the monitored impedances; and the first and second iterations are performed within a time period of less than 10 milliseconds.

A second illustrative and non-limiting example takes the form of a signal generator adapted for use in delivery of tissue ablation energy comprising: a therapy output block including to a voltage conversion circuit, an energy storage circuit and an output control circuit; an input/output circuit adapted to couple to a probe for delivery of tissue ablation energy, the input/output circuit defining a plurality of output channels such that a probe coupled thereto and having a plurality of electrodes can be used with separate activation of subsets of the plurality of electrodes; a user interface allowing a user to control the signal generator and adapted to display one or more parameters of tissue ablation energy to be delivered by the signal generator; a controller coupled to the therapy output block and the user interface; a memory coupled to the controller and having stored instructions for the delivery of a treatment cycle, the treatment cycle comprising: a first pulse train comprising first pulses of a first polarity having a first amplitude and a first pulse width, alternating with second pulses of a second polarity opposite the first polarity, having a second amplitude and having a second pulse width less than the first pulse width; a second pulse train comprising third pulses of the first polarity having a third amplitude and a third pulse width, alternating with fourth pulses of the second polarity having a fourth amplitude and a fourth pulse width greater than the third pulse width; such that the first pulse train yields a first charge imbalance, and the second pulse train yields a second charge imbalance that offsets the first charge imbalance to prevent muscle stimulation.

Additionally or alternatively to the second illustrative example, the stored instructions may define the first and second amplitudes to be equal, and the third and fourth amplitudes to be equal.

Additionally or alternatively to the second illustrative example, the stored instructions may require delivery of the first and second pulse trains in sequence such that a time from the start of the first pulse train to the end of the second pulse train is less than one millisecond.

Additionally or alternatively to the second illustrative example, the stored instructions may define the first and fourth pulse widths as equal in duration, and the second and third pulse widths as equal in duration.

Additionally or alternatively to the second illustrative example, the stored instructions may define the first pulse train to comprise a first quantity of first pulses and a second quantity of second pulses, and the second pulse train to comprise a third quantity of third pulses and a fourth quantity of fourth pulses, wherein the first, second, third and fourth quantities are all equal.

Additionally or alternatively to the second illustrative example, the stored instructions may define the first pulse widths as twice the second pulse widths, and the fourth pulse widths as twice the third pulse widths.

Additionally or alternatively to the second illustrative example, the stored instructions may define the first, second, third and fourth amplitudes to each exceed an irreversible electroporation threshold.

Additionally or alternatively to the second illustrative example, the stored instructions may define the first, second, third and fourth pulse widths each in a range of about 0.1 to 500 microseconds.

Another illustrative and non-limiting example takes the form of a system comprising a signal generator as in any of the first or second illustrative, non-limiting examples, and alternatives or additions thereto, along with a probe adapted for use with the signal generator, the probe having a plurality of ablation therapy delivery electrodes thereon.

A third illustrative and non-limiting example takes the form of a method of delivering a multiphasic ablation waveform comprising: generating a first output of a first polarity at a first amplitude for a first time period as a first phase; generating a second output of a second polarity, opposite the first polarity, at a second amplitude for a second time period, the second time period being less than half the first time period; and generating a third output using the second polarity at a third amplitude less than the second amplitude for a third time period, the third time period being greater than the first time period; wherein the sum of the first, second and third outputs yields a balanced charge to limit muscle stimulation associated with the multiphasic ablation waveform.

Additionally or alternatively to the third illustrative example, at least one of the first and second amplitudes may exceed an irreversible electroporation threshold, and the third amplitude may be less than an irreversible electroporation threshold.

Additionally or alternatively to the third illustrative example, at least one of the first and second amplitudes may exceed an irreversible electroporation threshold, and the third amplitude may be less than a reversible electroporation threshold.

Additionally or alternatively to the third illustrative example, one of the first, second and third time periods may exceed the sum of the other two of the first, second and third time periods.

Additionally or alternatively to the third illustrative example, the first time period may be in the range of about 1 to 50 microseconds, and the second time period may be in the range of about 0.5 to 10 microseconds.

Additionally or alternatively to the third illustrative example, the first, second and third time periods may add up to a duration of less than one millisecond.

Another illustrative and non-limiting example may comprise in a first iteration, performing the method of the third illustrative and non-limiting example while monitoring one or more of impedance of current flow for each of the first, second and third outputs; and in second iteration, again performing the method of the third illustrative and non-limiting example, and adjusting at least one of the amplitude or pulse width of at least one of the first, second and third outputs to reduce change imbalance, if any, resulting from the monitored impedances; wherein the first and second iterations are performed within a time period of less than 10 milliseconds.

A fourth illustrative and non-limiting example takes the form of a method of delivering a multiphasic ablation waveform comprising: generating a first pulse train comprising first pulses of a first polarity having a first amplitude and a first pulse width, alternating with second pulses of a second polarity opposite the first polarity, having a second amplitude and having a second pulse width less than the first pulse width; generating a second pulse train comprising third pulses of the first polarity having a third amplitude and a third pulse width, alternating with fourth pulses of the second polarity having a fourth amplitude and a fourth pulse width greater than the third pulse width; such that the first pulse train yields a first charge imbalance, and the second pulse train yields a second charge imbalance that offsets the first charge imbalance to prevent muscle stimulation.

Additionally or alternatively to the fourth illustrative example, the first and second amplitudes may be equal, and the third and fourth amplitudes may be equal.

Additionally or alternatively to the fourth illustrative example, the first and second pulse trains may be delivered in sequence such that a time from the start of the first pulse train to the end of the second pulse train is less than one millisecond.

Additionally or alternatively to the fourth illustrative example, the first and fourth pulse widths may be equal in duration, and the second and third pulse widths may be equal in duration.

Additionally or alternatively to the fourth illustrative example, the first pulse train may comprise a first quantity of first pulses and a second quantity of second pulses, and the second pulse train may comprise a third quantity of third pulses and a fourth quantity of fourth pulses, wherein the first, second, third and fourth quantities are all equal.

Additionally or alternatively to the fourth illustrative example, the first pulse widths may be twice the second pulse widths, and the fourth pulse widths may be twice the third pulse widths.

Additionally or alternatively to the fourth illustrative example, the first, second, third and fourth amplitudes may each exceed an irreversible electroporation threshold.

Additionally or alternatively to the fourth illustrative example, the first, second, third and fourth pulse widths may each be in a range of about 0.1 to 500 microseconds.

A fifth illustrative and non-limiting example takes the form of a method of delivering a multiphasic ablation waveform comprising: generating a first pulse of a first polarity having a first amplitude and a first pulse width; generating a first pulse train having a plurality of second pulses of a second polarity opposite the first polarity, the second pulses having second amplitudes and second pulse widths, the second pulse widths being less than ½ of the first pulse width; such that the first pulse yields a first charge imbalance, and the second pulse train yields a second charge imbalance that offsets the first charge imbalance to prevent muscle stimulation.

Additionally or alternatively to the fifth illustrative example, the plurality of second pulses may each be separated by an interpulse interval, the interpulse interval being between one-half and twice the second pulse width.

Additionally or alternatively to the fifth illustrative example, the first pulse width may be equal to a sum of the second pulse widths.

Additionally or alternatively to the fifth illustrative example, the first amplitude and the second amplitude may each exceed an irreversible electroporation threshold.

Additionally or alternatively to the fifth illustrative example, the first amplitude may be less than the second amplitude; and the sum of the second pulse widths may be less than the first pulse width.

Additionally or alternatively to the fifth illustrative example, the second pulses may be each separated by an interpulse interval, wherein the sum of the second pulse widths and the interpulse intervals is equal to the first pulse widths.

Additionally or alternatively to the fifth illustrative example, a duration from the start of the first pulse to the end of the first pulse train may be less than one millisecond.

A sixth illustrative and non-limiting example takes the form of a method of delivering a multiphasic ablation waveform comprising: delivering a first pulse train comprising a plurality of first pulses each having a pulse width and an amplitude, wherein a first in time of the first pulses has a first amplitude, and each successive pulse of the first pulses has a larger amplitude than an immediately preceding pulse, each of the first pulses having a first polarity; delivering a second pulse train comprising a plurality of second pulses each having a pulse width and an amplitude, wherein a first in time of the second pulses has the first amplitude, and each successive pulse of the second pulses has a larger amplitude than an immediately preceding pulse, each of the second pulses having a second polarity opposite of the first polarity; wherein the first pulse train and second pulse train are delivered within a time window of less than about one millisecond, such that charge balance is achieved upon conclusion of the second pulse train.

Additionally or alternatively to the sixth illustrative example, within the first pulse train, the first in time pulse may have an amplitude that is less than an irreversible electroporation threshold, and the last in time pulse may have an amplitude that is greater than an irreversible electroporation threshold; and within the second pulse train, the first in time pulse may have an amplitude that is less than an irreversible electroporation threshold, and the last in time pulse may have an amplitude that is greater than an irreversible electroporation threshold.

Another illustrative and non-limiting example takes the form of a pulse generator configured for use with a probe for delivering ablation therapy to a patient, the pulse generator comprising output circuitry for delivering voltage-based therapy, monitoring circuitry for monitoring characteristics of delivered therapy pulses, and control circuitry comprising a non-volatile memory containing an executable instruction set adapted to deliver therapy as in any of the third to sixth illustrative examples and additions and alternatives thereto. Another example may be a system comprising such a pulse generator and a probe adapted for use with the pulse generator and comprising a plurality of therapy delivery electrodes.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 2-4 show various impacts of application of electrical field to a cell;

DETAILED DESCRIPTION

Figure 1:
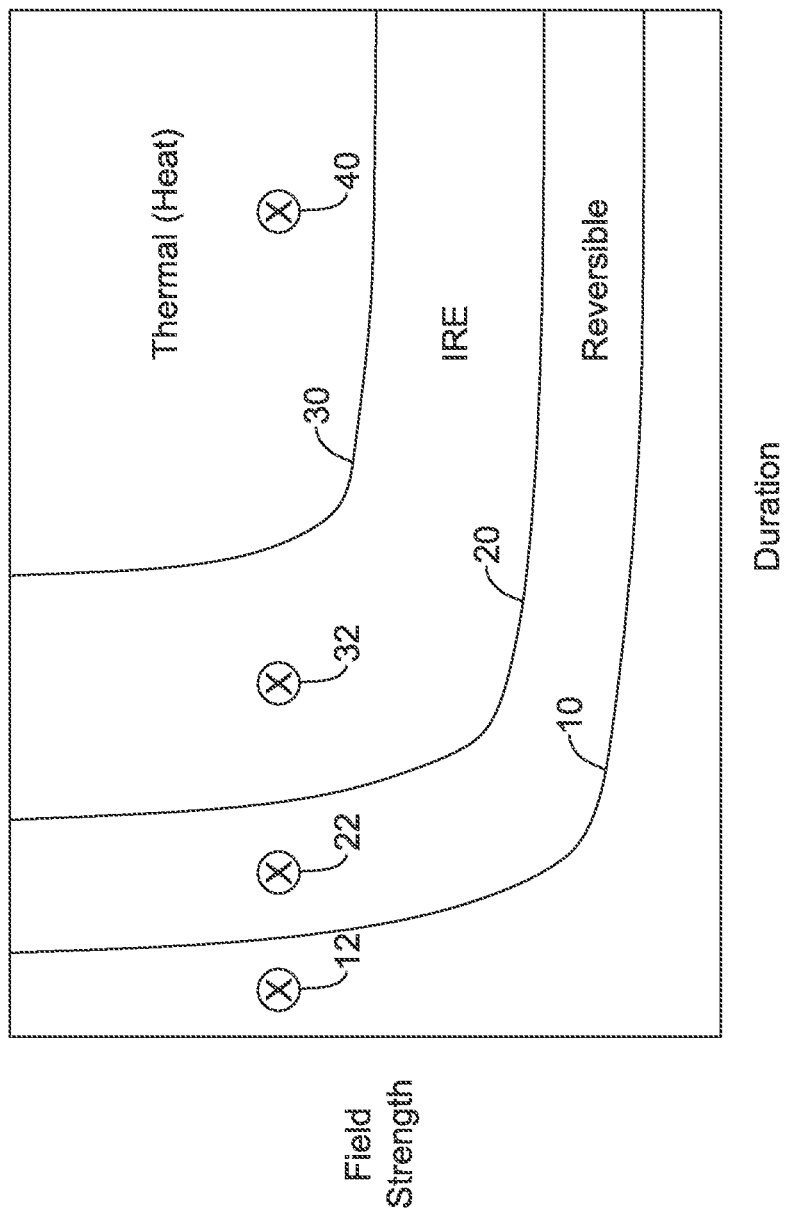
FIG. 1 shows an approximation of different therapy modalities associated with a combination of electrical field strength and pulse duration.

FIG. 1 shows an approximation of different biophysical responses dependent on the amplitude-time relationship of delivered electrical pulses. The thresholds between cellular responses (10, 20, 30) operate generally as a function of the applied field strength and pulse duration. Below a first threshold 10, no effect occurs; between the first threshold 10 and a second threshold 20, reversible electroporation occurs. Above the second threshold 20, and below a third threshold 30, primarily irreversible electroporation (IRE) occurs. Above a third threshold 30, the effects begin to be primarily thermal, driven by tissue heating. Thus, for example, at a given field strength and duration there may be no effect (location 12), and extending the duration of the field application can yield reversible electroporation (location 22), irreversible electroporation (location 32), and thermal ablation (location 40).

As described in U.S. Pat. No. 6,010,613, a transmembrane potential in the range of about one volt is needed to cause reversible electroporation, however the relationship between pulse parameters, such as timing and duration, and the transmembrane potential required for reversible electroporation remains an actively investigated subject. The required field may vary depending on characteristics of the cells to be treated. At a macro level, reversible electroporation requires a voltage in the level of hundreds of volts per centimeter, with irreversible electroporation requiring a still higher voltage. As an example, when considering in vivo electroporation of liver tissue, the reversible electroporation threshold field strength may be about 360 V/cm, and the irreversible electroporation threshold field strength may be about 680 V/cm, as described in U.S. Pat. No. 8,048,067. Generally speaking, a plurality of individual pulses are delivered to obtain such effects across the majority of treated tissue; for example, 2, 4, 8, 16, or more pulses may be delivered. Some embodiments may deliver hundreds of pulses.

The electrical field for electroporation has typically been applied by delivering a series of individual pulses each having a duration in the range of one to hundreds of microseconds. For example, U.S. Pat. No. 8,048,067 describes analysis and experiments performed to illustrate that the area between lines 20 and 30 in FIG. 1 actually exists, and that a non-thermal IRE therapy can be achieved, using in several experiments a series of eight 100 microsecond pulses delivered at 1 second intervals.

The tissue membrane does not return instantaneously from a porated state to rest. As a result, the application of pulses close together in time can have a cumulative effect as described, for example, in U.S. Pat. No. 8,926,606. In addition, a series of pulses can be used to first create pores in a cell membrane and then move large molecules through generated, reversible pores, with electric field serving both to maintain the pores and to move the molecules as described in US PG Patent App. Pub No. 2007/0025919.

FIGS. 2-4 show various impacts of application of electrical field to a cell. At electric field strengths below the threshold for reversible electroporation, as shown in FIG. 2, the cell membrane 62 of cell 60 remains intact and no pores occur. As shown in FIG. 3, at a higher electric field strength, above the threshold for reversible electroporation and below the threshold for irreversible electroporation, the membrane 72 of cell 70 develops pores 74. Depending on the characteristics of the applied field and pulse shapes, larger or smaller pores 74 may occur, and the pores developed may last for longer or shorter durations.

As shown in FIG. 4, at a still higher electric field strength, above the threshold for irreversible electroporation, the cell 80 now has a membrane 82 with a number of pores 84, 86. At this higher amplitude or power level, pores 84, 86 may become so large and/or numerous that the cell cannot recover. It may be noted as well that the pores are spatially concentrated on the left and right side of the cell 80 as depicted in FIG. 4, with few or no pores in the region 88 where the cell membrane is parallel to the applied field (assuming here that the field is applied between electrodes disposed to the right and left sides of the cell shown in FIG. 4). This is because the transmembrane potential in region 88 remains low where the field is closer to parallel, rather than orthogonal, to the cell membrane.

Figure 5:
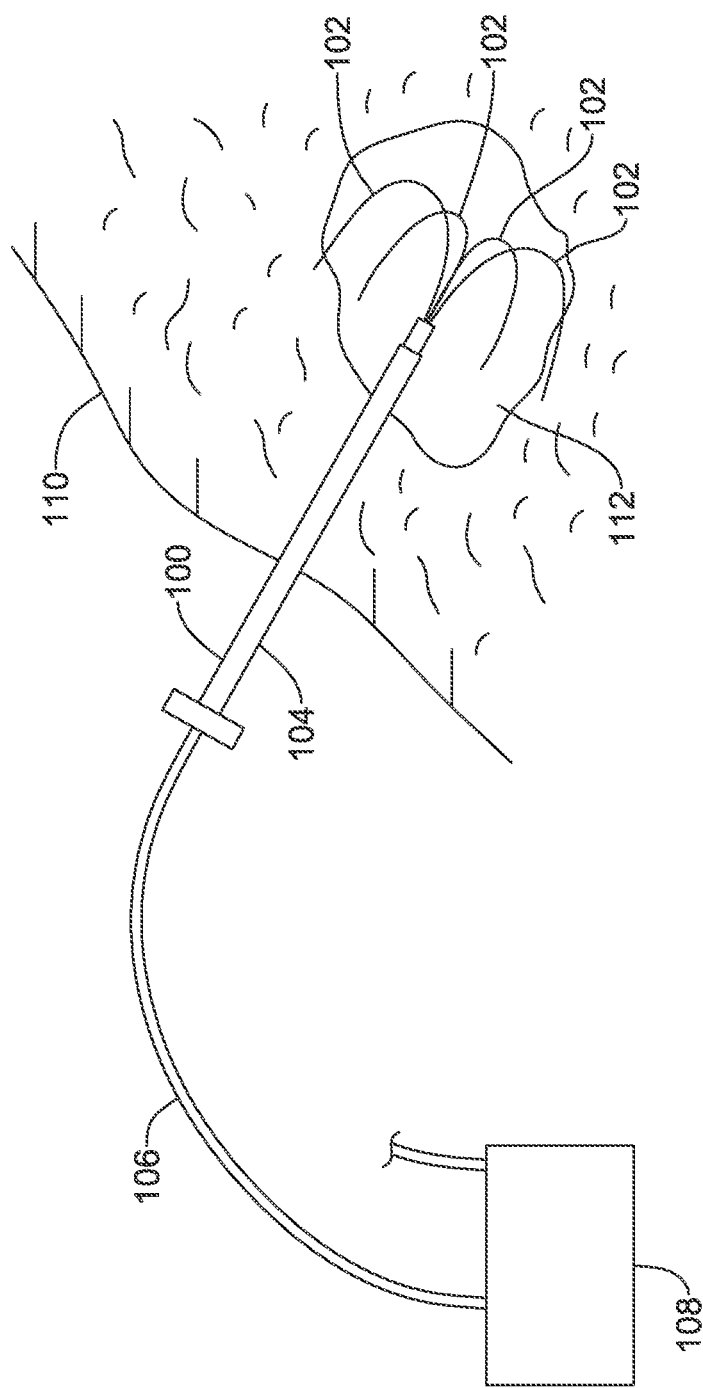
FIG. 5 shows a prior art "Leveen" needle.

FIG. 5 shows a prior art "Leveen" needle, which may be used as a probe to deliver therapy. As described in U.S. Pat. No. 5,855,576, the device comprises an insertable portion 100 having a shaft 104 that extends to a plurality of tissue piercing electrodes 102 that can be extended or retracted once a target tissue 112 of a patient 110 is accessed. The proximal end of the apparatus is coupled by an electrical connection 106 to a power supply 108, which can be used to supply RF energy.

Conventionally, the Leveen needle would be used to deliver thermal ablation to the target tissue. For example, as described in the '576 patent, a return electrode in the form of a plate or plates may be provided on the patient's skin, a return electrode could be provided as another tissue piercing electrode, or a return electrode may be provided on the shaft 104 near its distal end, proximal of the tissue piercing electrodes 102.

Enhancements on the original design can be found, for example, in U.S. Pat. No. 6,638,277, which discusses independent actuation of the tissue piercing electrodes 102, both in terms of movement of the electrodes as well as separately electrically activating individual ones of the electrodes. The U.S. Pat. Nos. 5,855,576 and 6,638,277 patents are incorporated herein by reference for showing various therapy delivery probes. U.S. Provisional Patent Application Ser. No. 62/620,873, the disclosure of which is incorporated herein by reference as showing various therapy delivery probes, discloses updates and enhancements on the Leveen needle concept, allowing flexibility in the spacing, size and selection of electrodes.

Figure 6:
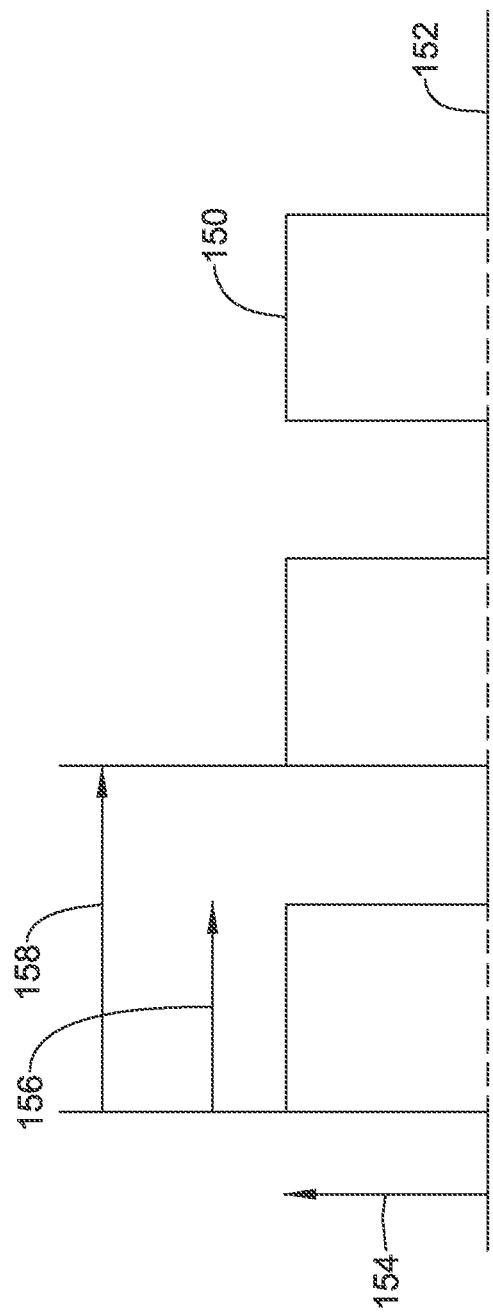
FIGS. 6-8 show various waveform features.
Figure 7:
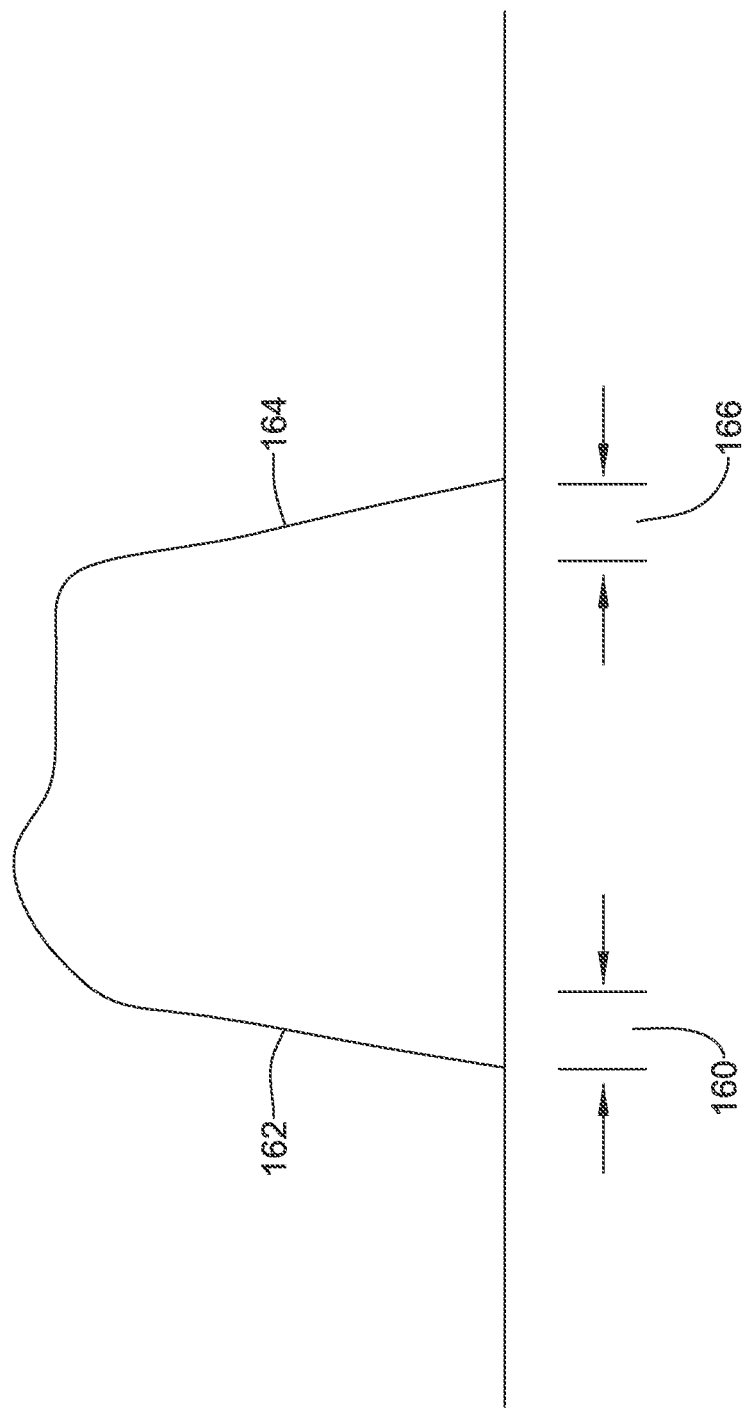
Figure 8:
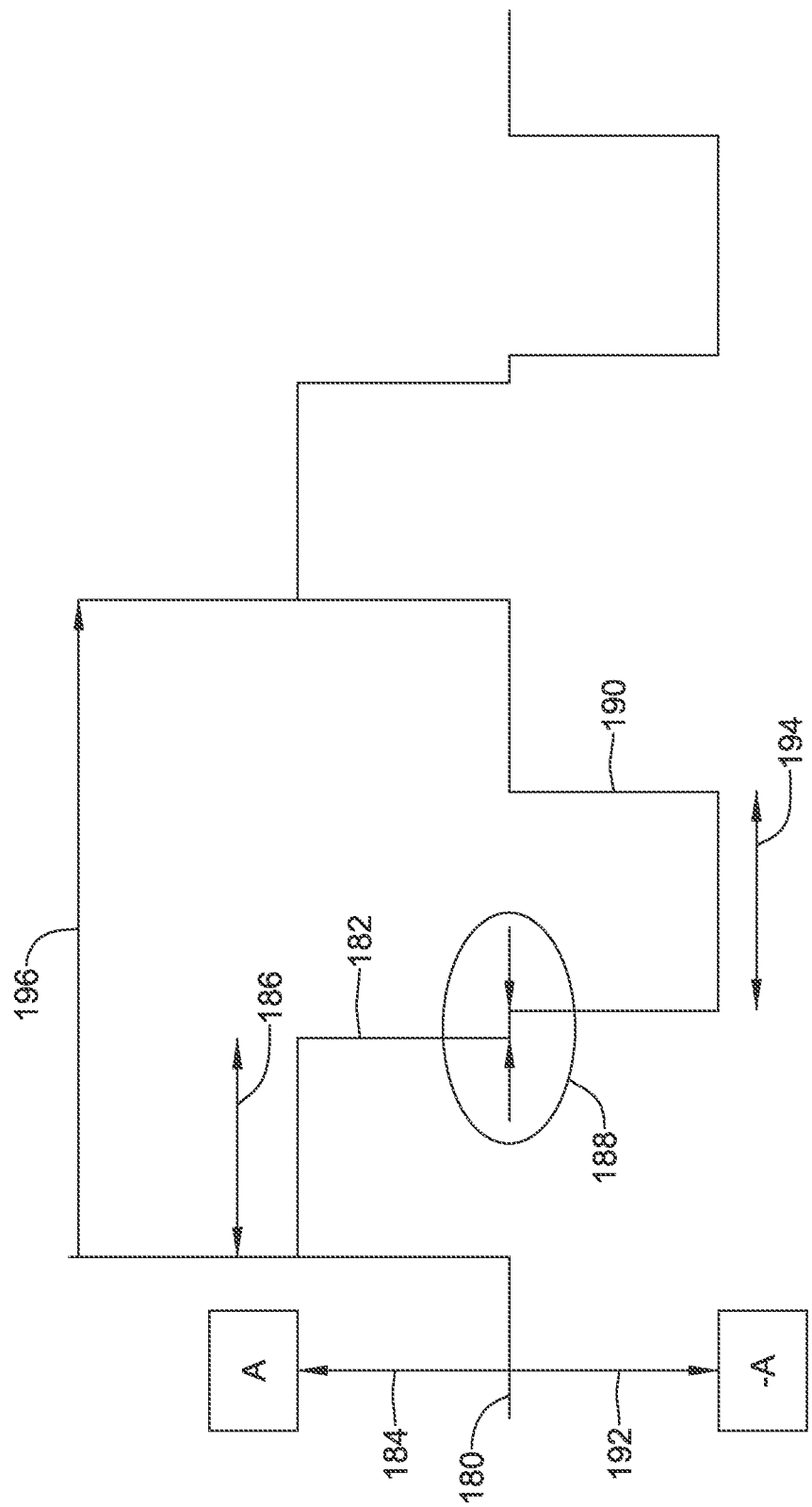

FIGS. 6-8 show various waveform features. Referring to FIG. 6, a monophasic waveform is shown at 150. The waveform 150 is shown relative to a baseline or equipotential 152. An idealized square wave is shown having an amplitude 154, a pulse width 156, and a cycle length 158. The waveform 150 is shown as an ideal square wave, with a vertical upswing from baseline 152 to the designated amplitude 154. When describing such a waveform, the frequency typically refers to the inverse of the cycle length 158. So, for example, if a waveform having a one microsecond pulse width 156 is delivered at two microsecond intervals 158, the "frequency" of the waveform may be described as 500 kHz (the inverse of two microseconds). The waveform 150 may be a current controlled or voltage controlled waveform. Either approach may be used in various examples, as further described below.

In any real application the edges of the generated waveform will be rounded and the upswing from baseline 152 will be more as shown in FIG. 7, where the upward divergence from the baseline, shown at 162, is characterized by a rise time 160. At the end of the output, there is also a non-ideal fall 164 characterized by fall time 166. Real application of the waveform will also include some variation in the peak amplitude, as shown, which may include for example overshoot of the amplitude if the signal output is underdamped, or rounding off of the edges for a critically damped or overdamped signal.

In some examples, one or more of the rise or fall time 160, 166 can be manipulated. In an illustrative example, the output circuitry of a system may include selectable elements, such as resistors, inductors or the like, that can slow the rise time if switched into the circuit. For example, the current through an inductor cannot be instantaneously changed, so switching an inductive element into an output circuit can slow the rise time as the inductor begins to allow current to flow.

Rise and fall time may be manipulated in several different ways. For example, the process settings may be selected to modify the peak voltage target; a higher target can yield a faster rise time as various components respond in exponential fashion to being turned on or switched into an output circuit. By monitoring the output, the system can artificially increase a peak voltage target to reduce rise time, and once the true peak voltage is met, the system may switch voltage sources or use an output regulation (such as by using a rectifier or by redirecting output current through a separate discharge path) to cap the voltage output. In another example, component selection may be used, such as by having a plurality of different HV switches available and selectable to the system, with different HV switch types having different rise and fall times. For example, if three output switches are available, each with a different rise/fall characteristic, the system may respond to a user input requesting longer or shorter rise/fall time by selecting an appropriate output switch for use during a particular therapy output session. High pass or low pass filtering may be switched into the output circuit as well to control slew rate, or may be switched into the control signal circuit; a slow turn-on of an output transistor for example can cause slower rise time for the transistor itself and conversely fast turn-on of the output transistor can speed the rise time. In another example, a digital to analog converter may be used as an output circuit, allowing digitized control of rise or fall time. In still a further example, control signals to the output switches can be generated by a digital to analog converter, thus manipulating the on/off signal to the output circuitry itself. In still a further example, using a capacitor stack output as shown in U.S. Provisional Patent Application 62/819,101, filed Mar. 15, 2019 and titled WAVEFORM GENERATOR AND CONTROL FOR SELECTIVE CELL ABLATION (the disclosure of which is incorporated herein by reference), a fast rise time may be effected by using a single switched output from the top (or desired target level) of the capacitor stack, while a slow rise time may be effected by sequentially turning on an output using less than all of the capacitor stack and then subsequently adding more of the capacitor stack to the output; appropriately placed diodes in the output circuitry will prevent back-current or shorting of the newly added portions of the capacitor stack during such a maneuver.

FIG. 8 shows further details, this time for a biphasic signal. Here, the waveform is shown at 180, with a first, positive pulse at 182 quickly followed by a negative pulse at 190. The positive pulse 182 has an amplitude 184, and the negative pulse 190 has an amplitude 192 which is usually equal in voltage to, but of opposite polarity than, the positive pulse. The positive pulse 182 has a pulse width 186, and the negative pulse 190 has a pulse width 194; again, typically the two pulse widths 186, 194 would be equal to one another. For a signal as shown, the cycle length can be determined as shown at 196, from the start of the positive pulse 182 to the initiation of a subsequent cycle; again, frequency is the inverse of the cycle length.

In a typical application or use of biphasic signals, the aim is, in part, to achieve charge balancing at the end of each cycle. For that reason, the pulse widths of the two phases are kept equal, and the amplitudes are also equal though of opposite polarity. Whether using a voltage controlled or current controlled system, charge balance can be reasonably maintained by controlling just the pulse width and amplitude. For example, in a voltage controlled system, the current flow will be more or less constant within a cycle, assuming the cycle length 196 is in the millisecond range or less. That is, while it is known that during ablation procedures the tissue impedance changes as cells are destroyed, expelling cellular media which generally reduces impedance, the impedance does not change so quickly that a simple biphasic waveform would fail to provide charge balance.

An interphase period 188 represents a time period spent at baseline between the positive and negative pulses, and is ordinarily minimized in accordance with the physical constraints of the underlying circuitry. Thus, for example, if a first switch must turn off to end the positive pulse 182, and a second switch is used to initiate the negative pulse 190, assuming digital control, the system may allow a few digital clock cycles to expire after turning off the first switch before turning on the second switch, to avoid any possible internal shorting. Faster switches can reduce the interphase time, and much engineering effort has gone into reducing this time period 188.

For example, a very short interphase period 188 can be achieved using a design as shown in U.S. Pat. No. 10,154,869. In the 10,154,869 patent, an inductor is placed in parallel with the output load. A power source is applied to the load and inductor during an initial phase of therapy delivery. Opening a switch between the power source and the load/inductor causes a near immediate reversal of current through the load as the inductor draws current from the load after the power source is disconnected.

The background to be gathered from FIGS. 6-8 is that of typical usage. In several embodiments described further below, monophasic pulses are used to achieve biphasic results with respect to charge balancing that prevents muscle stimulation. It should be noted that within all the examples herein, the term "without causing muscle stimulation" allows for some muscle stimulation, but only an amount tolerable within the relevant intervention and/or surgical domain. For example, the stimulation that occurs is not so much that the patient is made uncomfortable. In another example, the stimulation that occurs is small enough that surgery to ablate tissue is not subject to interference due to stimulated patient movement. In another example, the muscle stimulation that occurs is insignificant to the surgery and allows surgery to be performed without requiring administration of a paralytic. In some examples, the stimulation that occurs does not affect probe placement and securement, or is small enough that migration of the probe does not occur.

Figure 9:
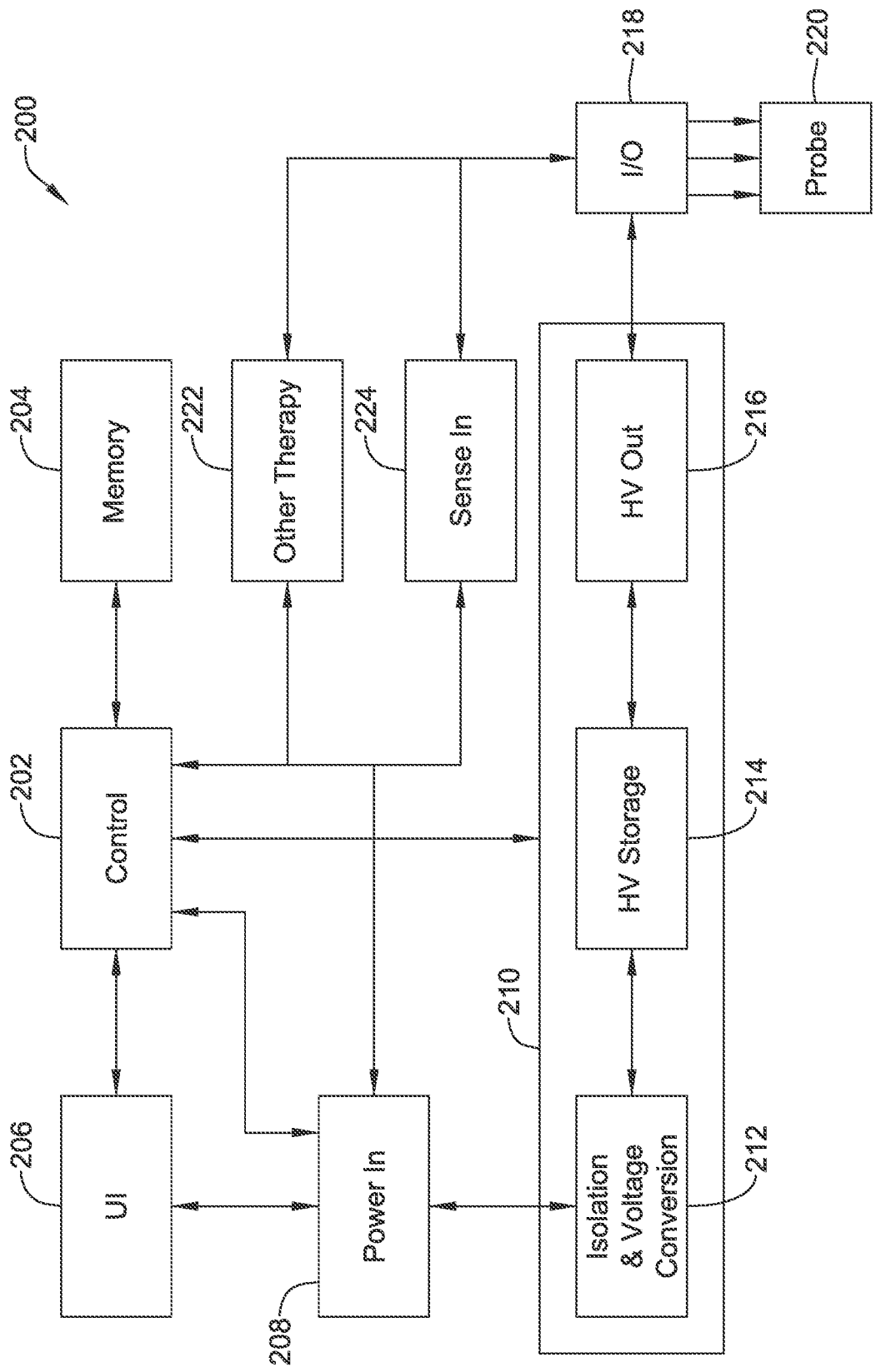
FIG. 9 shows a signal generator in block form.

FIG. 9 shows a signal generator in block form. A signal generator 200 may be a self-contained unit, or it may comprise several discrete components coupled together with wires and/or wireless connections. A control block is shown at 202 and may comprise a plurality of logic circuits in the form of a state machine, a microcontroller and associated digital logic, or a microprocessor, or even an off the shelf computing unit such as a laptop or desktop computer, as desired. A memory 204, which may or may not be separate from the control block 202, is included to store executable instruction sets for operation as well as keeping a log of activity of the system and any sensor outputs received during therapy. The memory 204 may be a volatile or non-volatile memory, and may include optical or digital media, a Flash drive, a hard drive, ROM, RAM, etc. A UI or user interface 206, which may also be integrated with the control block (such as when using a laptop for control 202, which would include each of memory 204 and a UI 206). The UI 206 may include a mouse, keyboard, screen touchscreen, microphone, speakers, etc. as desired.

Power in 208 may include a battery or batteries, and will typically include an electrical coupling to plug into a wall socket to receive line power. A therapy block is shown at 210 and includes several stages. An isolation and voltage conversion circuit is shown at 212 and may include, for example, one or more transformers or other step-up converters (such as a capacitive step-up conversion circuit) to take a battery or line voltage and increase to a high voltage output that is stored in HV storage 214. The HV storage 214 may include batteries, inductors or other circuit elements, but will typically be a capacitive storage block such as a stack of capacitors. HV storage 214 may be helpful to take the HV signal from block 212 and smooth it out over time to provide a more stable high voltage output that is then delivered by an HV output circuit 216. Also, the HV storage 214 may enable a lower power voltage input to generate very high power outputs by storing energy over a longer period of time to be delivered in short bursts.

The HV output circuit 216 may serve as an output control circuit. The HV output circuit may include a number of switches and other elements, including for example, high voltage switches such as silicon controlled rectifiers, high power Mosfets, and other elements, allowing selective outputting of the high voltage signal to an IO block shown at 218. The IO block 218 may provide a number of sockets to receive plugs from one or more delivery probes 220, as well as one or more outputs for one or more indifferent electrodes to be placed on the body of a patient, serving as return electrodes or simply grounding the patient and system.

In some alternative approaches to the therapy block 210, rather than HV Out 216 using sets of switches to directly output a signal from HV storage, a resonant circuit may be powered by the HV signal, with outputs of the resonant circuit used for therapy delivery by selectively switching the output of the resonant circuit. A topology that uses a set of four switches in an "H-bridge" to drive an RF circuit is shown, for example, in U.S. Pat. No. 10,105,172. In some embodiments, control over the individual pulses is achieved in the present invention by omitting the driven RF circuit and simply relying on a form of extended H-bridge circuit, as shown in U.S. Provisional Patent Application 62/819,101, filed Mar. 15, 2019 and titled WAVEFORM GENERATOR AND CONTROL FOR SELECTIVE CELL ABLATION, the disclosure of which is incorporated herein by reference.

One or more sensing circuits 224 may be included to provide feedback to the control block 202. For example, the sensing circuits may measure voltage at the output nodes to the probe 220, or may measure current going to the output nodes that couple to the probe 220, allowing tissue characteristics to be monitored. For example, voltage measuring circuits are well known in the art, including, for example, direct-conversion, successive approximation, ramp-compare, Wilkinson, integrating, Delta-encoded, pipelined, sigma-delta, and/or time-interleaved ADC, any of which may be used as suited to the application. Current measuring circuitry may use, for example, trace resistance sensing, a current sensor based on Faraday's Law such as a current transformer or Rogowski coil, or the use of magnetic field sensors (Hall effect, Flux gate, and/or a magneto-resistive current sensor) electrically or magnetically coupled to one or more transmission lines. Current sensing of the output circuitry may be used for safety purposes to prevent or limit shorting or overcurrent conditions, for example.

In another example, the probe 220 may include a sensor, such as a temperature sensor, a force sensor, or a chemical or pH sensor, any of which can be used to monitor tissue characteristics during therapy delivery. For example, a temperature sensor may be used to manage a non-thermal therapy such as electroporation by observing whether the temperature in a region is raising above a threshold temperature or showing an increasing trend, in which case one or more elements of power output may be reduced to ensure that the desired therapy type is dominant. If the probe contains such items, the sensing circuits 224 may include any suitable amplifier, filter or the like to allow the sensed signal to be conditioned for use by the control block 202.

Sensing circuits 224 may include a cardiac rhythm sensor that is adapted for use with one or more electrodes (such as surface electrodes placed on the patient's chest) to capture cardiac rhythms and identify physiological windows for therapy deliver, as discussed below. A cardiac signal for purposes of identifying a physiological window for therapy may be received instead from an in-clinic ECG monitor, an implantable medical device such as a cardiac monitor, pacemaker or defibrillator, or from a variety of wearable products that sense cardiac rhythms.

Optionally, "other therapy" block 222 may be included. "Other" therapy may include, for example, the delivery of a chemical or biological agent to provide additional therapy, to enhance therapy being delivered, or to trigger immune response to facilitate the body healing itself after ablation. Such other therapy 222 may comprise a reservoir (which may be refillable) of material to be delivered to a patient via, for example, a syringe or catheter or through a probe. An "other therapy" 222 may include introducing a substance that enhances, augments, is synergistic with, or independently adds to the ablation effects of therapy delivered electrically. For example, a substance may be injected to modify or enhance electric field effects, as disclosed in U.S.

Pat. No. 11,045,648, titled IRREVERSIBLE ELECTROPORATION THROUGH A COMBINATION OF SUBSTANCE INJECTION AND ELECTRICAL FIELD APPLICATION, the disclosure of which is incorporated herein by reference.

In some examples, a cryotherapy may be integrated into the system to allow tissue cooling before, during or after electrical ablation, prompting immune response if desired. Cryotherapy may be delivered using, for example, a balloon on a therapy probe 220 or provided separately with a nozzle in the balloon coupled to a pressurized fluid source, such as nitrous oxide; the pressurized fluid when expelled through the nozzle will expand or go through a phase change from liquid to gas, which causes localized cooling, as disclosed for example in U.S. Pat. No. 6,428,534. In another example, a fluid (gas or liquid) may be externally cooled and introduced via a catheter for cryogenic purposes, or, in the alternative, externally heated and introduced via a catheter for heat ablation purposes.

In still other examples, other therapy 222 may include delivery of energy such as mechanical energy (ultrasound, for example) or optical energy using, for example, a laser source (such as a vertical cavity surface emitting laser) coupled to an optical fiber that extends through a probe to allow laser energy to be delivered to targeted tissue. In some examples, a secondary or "other" therapy may be used, as noted, to trigger the immune response even if it is not used as a primary approach for destroying targeted tissue.

In several examples, a biphasic effect reducing or minimizing muscle stimulation is achieved while separating positive and negative phases of a signal in time to provide for monophasic therapeutic effects. Therapy may be delivered using one or more pulse trains that meet each of two rules:

Charge balance rule: the pulse train is completed thereby providing charge balance or an approximation of charge balance within:
  A time period that is less than the time constant of surrounding tissue, which can depend on factors such as tissue type and water content. The time constant of surrounding tissue reflects the complex impedance of the tissue and cells in the electrical field. For example, the time constant of the tissue between two electrodes would be determined by the complex impedance thereof; in a simplified model the time constant would be the capacitance multiply the resistance of the tissue, including cells, within the electrical field that would be generated between two electrodes. Cells or tissue which is already polarized may have a greater or lesser effective time constant.
  A time period of less than about one millisecond
  A maximum time period tolerable for the patient, as determined by testing the patient. For example, to test a patient, a therapy output may include first and second portions separated by a period of time, and the period separating the first and second portions can be extended until muscle contraction is observed, until the patient reports feeling a contraction or tension, or until discomfort is indicated by the patient, wherein the first portion of the therapy is a first monophasic pulse or pulses that impart a charge imbalance, and the second portion of the therapy is configured to remove the charge imbalance. For example, a biphasic output may be separated into two portions by controlling and expanding the interphase period (FIG. 8, 188) to a multiple of the pulse width—such as using 5 microsecond pulses separated by tens or hundreds of microseconds, or even more, out to several milliseconds, as tolerated by the patient and while still staying within the therapy completion rule noted below.

Therapy completion rule: the pulse train is to be delivered within a physiological window determined by observation of a non-therapy factor, such as the cardiac rhythm of the patient.

Regarding the therapy completion rule, using the heart as the driver, the cardiac rhythm contains various components known by convention as the R-wave, QRS complex, P-wave, and T-wave. Stimulus of non-cardiac tissue for ablation purposes ought not interfere with the cardiac rhythm, and the heart may be less susceptible to electrical signal interference in an interval between the R-wave peak (or end of the QRS complex) and the T-wave. Sometimes this interval can be called the S-T interval (the S-wave ends the QRS complex); the S-T interval for a given patient is likely to last tens of milliseconds and may range from 5 to 100 milliseconds. Approximately 60 milliseconds is typical for a healthy individual, though it is noted that the therapies discussed herein are not necessarily for healthy or typical people and, therefore, the S-T interval may not be "typical". In an example, R-waves are sensed and therapy bursts are delivered after a delay of about 50 milliseconds from the R-wave detection or R-wave peak. In any event, in some examples, therapy is started and completed within the S-T interval window. A cardiac signal useful for identifying the S-T interval, or other physiologically useful window, may be obtained from a separate device (external or implantable) or may be sensed by a therapy generator having inputs for receiving cardiac signals from electrodes placed in or on the patient. Other sources may be the drivers; for example, detecting diaphragm movements may be useful as well, to time delivery of therapy for when the patient has inhaled, or exhaled.

In other examples, one, the other, or both of these timing rules may be omitted. In some examples, the windows may be approximated, such as by setting a rule that a pulse train must return to a balanced charge state in less than one millisecond, or 800 microseconds, or 500 microseconds.

Figure 10:
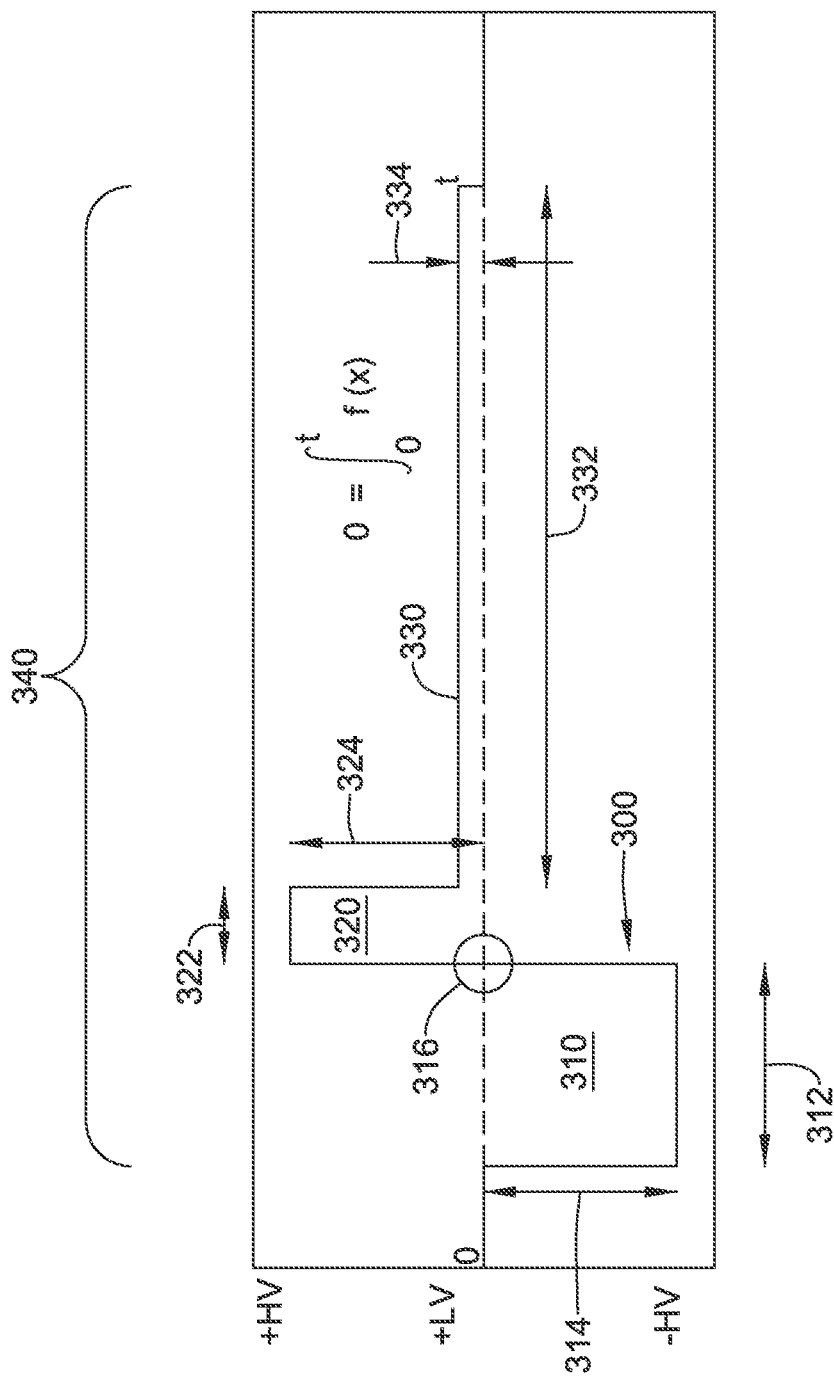
FIGS. 10-15 show various time multiplexed therapy patterns.

FIG. 10 shows an illustrative therapy waveform 300. This example illustrates a method of delivering a multiphasic ablation waveform comprising: generating a first output 310 of a first polarity (in the example show, pulse 310 has a negative polarity) at a first amplitude 314 for a first time period using pulse width 312, as a first phase. In the method, the next step is generating a second output 320 of a second polarity (here, positive polarity as shown), opposite the first polarity, at a second amplitude 324 for a second time period using pulse width 322, the second time period 322 being less than half the first time period 312. In an example, the second time period may be, for example, 1-5 microseconds, while the second time period is 10 microseconds, though other periods may be used. In some examples, the first time period or pulse width 312 may be in the range of about 1 to 50 microseconds, and the second time period or pulse width 322 may be in the range of about 0.5 to 10 microseconds. The method further includes generating a third output 330 using the second polarity (again a positive polarity is shown) at a third amplitude 334 less than the second amplitude for a third time period, shown as pulse width 332, the third time period being greater than the first time period. In the example the third time period may be, for example, in the range of about 10 to about 500 microseconds, as desired. Further in the example, the sum of the first, second and third outputs yields a balanced charge to limit muscle stimulation associated with the multiphasic ablation waveform. So, as indicated, the integral of the output current—which may be in this case approximately the integral of the voltage, during the entire time period 340, is approximately zero. In a numeric, and non-limiting, example, the first pulse width 312 may be about 10 microseconds, with a first amplitude 314 of 800 volts (8 millisecond-volts), the second pulse width 322 may be about 4 microseconds, with a second amplitude 324 of 800 volts (3.2 millisecond-volts), and the third pulse width 332 may be about 100 microseconds with a voltage of about 48 volts (4.8 millisecond-volts), a sequence which, assuming generally constant impedance during the total period 340, would yield a balanced charge outputs.

In some examples, the first and second amplitudes 314, 324 each exceed an irreversible electroporation threshold, and the third amplitude 334 is less than an irreversible electroporation threshold. For example, the first and second amplitudes may be in the range of about 700 to 5000 volts, or higher or lower, depending on the distance between the electrodes in use, recognizing that an IRE threshold may be defined in volts per unit distance, such as 670 volts per centimeter, while the third amplitude is half, or less than half, the amplitude of the first and second amplitudes, for example, or otherwise below an IRE threshold.

In some examples, the first and second amplitudes 314, 324 each exceed an irreversible electroporation threshold, and the third amplitude 334 is less than a reversible electroporation threshold. For example, when configuring therapy outputs, the distance between therapy electrodes may be estimated or known, using methods noted above. Then, the first and second amplitudes 314, 324 can be calculated to exceed an IRE threshold such as exceeding 670 volts/cm, while the third amplitude is calculated to be below a reversible threshold such as below 330 volts/cm. In other examples, the third amplitude may be more than a reversible electroporation threshold. Keeping the third amplitude higher may be useful to encourage pores that have opened during the first and/or second phases of therapy delivery 320, 330, to remain open for a longer period of time, or even grow and become irreversible.

Curves such as those shown in FIG. 1 may be useful to aid in the planning of therapy. It may be noted that the longer—or shorter—durations may determine what field strength is needed to achieve reversible, or irreversible, electroporation. While the examples may note that the amplitude is set above or below an electroporation threshold (whether reversible or not), it is to be understand that the meaning is that the amplitude, taken in light of pulse width, is above or below such a threshold. Thus reference to amplitude is not meant as an exclusive statement, and the relevant threshold for any of these examples is the threshold for field strength at a given pulse width.

In some examples, the third time period is greater than the sum of the first and second time periods. Such examples may help in providing the desired charge balance while mimicking the desired monopolar therapy approach. In some examples, the second time period may be well shorter than noted above, such as by using a second time period that is one-fourth, or one-tenth, the first time period.

In some examples, the first, second and third time periods add up to a duration of less than one millisecond. By ensuring that the total duration 340 is less than a millisecond, charge balancing can be achieved within a time frame that will avoid or reduce the likelihood of muscle stimulation.

In some examples, the first and second outputs 310, 320 are separated by an interphase period 316 of at least 10 nanoseconds, and the second and third outputs are not separated by an interphase period. In the drawing of FIG. 10, no interphase period is shown. Such an approach may be achieved by using a topology as shown in U.S. Pat. No. 10,154,869. In other examples, however, an interphase period 316, in which no output voltage is being generated, may have a duration in the range of 1 nanosecond out to tens or even hundreds of microseconds, keeping in mind the aim to achieve charge balancing within a time period of less than a few milliseconds. During interphase, the output electrodes may be subject to an open circuit, or may be grounded or tied to a reference voltage, if desired. Most often, however, the electrodes will be open-circuited and placed in a high impedance state.

In some examples, the waveform 300 may be delivered repeatedly in first and second iterations; third or more iterations may be used as well. In some such examples, a first iteration is performed using a set of parameters that are preset, with the outputs delivered while monitoring one or more of impedance or current flow for each of the first, second and third outputs 310, 320, 330. Then, in the second (and possibly subsequent) iterations, the method includes adjusting at least one of the amplitude or pulse width of at least one of the first, second and third outputs 310, 320, 330 to reduce change imbalance, if any, resulting from the monitored impedances. In some such examples, the first and second iterations are performed within a time period of less than 10 milliseconds, or a time period of less than 1 millisecond. For example, returning to the above numeric example, a total period 340 for therapy delivery was discussed using about 115 microseconds. If iterations start at 200 microsecond intervals, up to five iterations could be performed within a 1 millisecond window. As noted above, the window for repeated iterations can be longer, for example, to fit within an S-T cardiac cycle window, such as up to about 50 milliseconds or longer. Whether each iteration is adjusted using impedance or not, it is noted that the waveform as shown in FIG. 10 can be delivered repeatedly.

Figure 11:
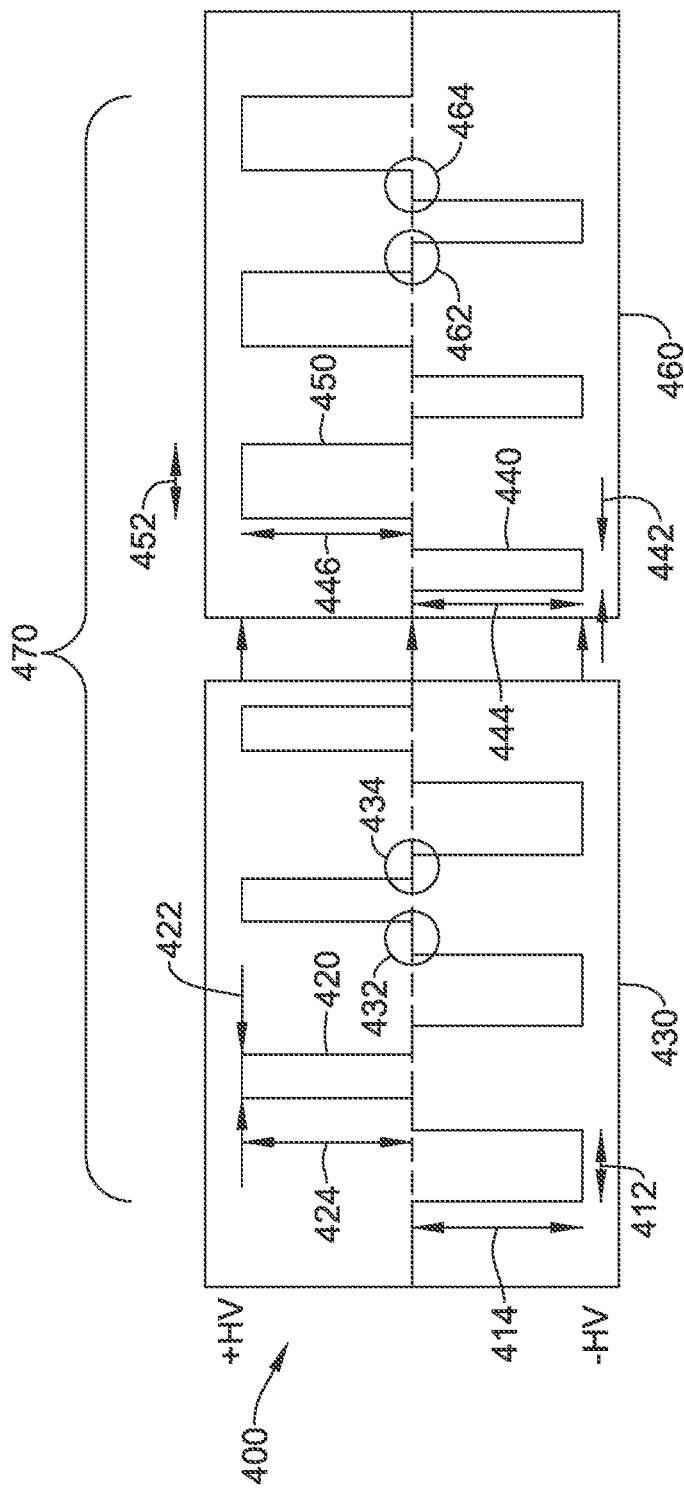

FIG. 11 shows an illustrative therapy waveform. This example shows a method of delivering a multiphasic ablation waveform comprising generating a first pulse train 430 comprising first pulses 410 of a first polarity (negative, in the illustration) having a first amplitude 414 and a first pulse width 412, alternating with second pulses 420 of a second polarity opposite the first polarity, having a second amplitude 424 and having a second pulse width 422 less than the first pulse width 412. The example further includes generating a second pulse train 460 comprising third pulses 440 of the first polarity having a third amplitude 444 and a third pulse width 442, alternating with fourth pulses 450 of the second polarity having a fourth amplitude 454 and a fourth pulse width 452 greater than the third pulse width 442. The example method may be performed such that the first pulse train 430 yields a first charge imbalance, and the second pulse train 460 yields a second charge imbalance that offsets the first charge imbalance to prevent muscle stimulation. The charge imbalance of the first pulse train 430 would be proportional to the difference between the product of amplitude 414, pulse width 412 and the quantity of first pulses 410 of the first pulse train 430, and the product of amplitude 424, pulse width 422, and the quantity of second pulses 420 of the first pulse train 430.

In some examples, the first and second amplitudes 414, 424 are the same, and the third and fourth amplitudes 444, 454 are the same. Further, the method may be performed such that a time 470 from the start of the first pulse train 430 to the end of the second pulse train 460 is short enough to avoid muscle stimulation due to the charge imbalance of the first pulse train 430. For example, time 470 may be shorter than one millisecond, or shorter than two milliseconds, or some other duration, as desired. In some examples, the first and fourth pulse widths 412, 452 are equal in duration, and the second and third pulse widths 422, 442 are equal in duration. For example, the first and fourth pulse widths 412, 452 may be in the range of about 1 to about 20 microseconds, and the second and third pulse widths 422, 442 may be in the range of about 0.1 to about 10 microseconds. In some examples, the first pulse width 412 is about double the second pulse width 422, and the fourth pulse width 452 is about double the third pulse width 442. In other examples, the first, second, third and fourth pulse widths are each in a range of about 0.1 to 50 microseconds and may have other suitable ratios. In general, the concept is to provide two pulse trains, each of which would be imbalanced if delivered alone, with delivery taking place in a short enough period of time to achieve charge balance without muscle stimulation.

In some examples, the first pulse train 430 comprises a first quantity of first pulses 410 and a second quantity of second pulses 420, and the second pulse train 460 comprises a third quantity of third pulses 440 and a fourth quantity of fourth pulses 450, wherein the first, second, third and fourth quantities are all equal.

In some examples, the first, second, third and fourth amplitudes each exceed an irreversible electroporation threshold. As noted, the "threshold" may be in part dependent on pulse width as well as the distances between electrodes. In other examples, the first, second, third and fourth pulse widths are each in a range of about 0.1 to 500 microseconds.

In an alternative formulation, a pulsetrain 430 may comprise an odd number of pulses, such as pulses p1 to p5, each having the same amplitude, in which pulses p1, p3 and p5 are of the same polarity and each have a pulse width PW, while pulses p2 and p4 are of opposite polarity and each have pulse width 1.5×PW, which would yield a charge balanced output even though pulses delivered in each polarity are unequal in charge content. In another example, a pulsetrain 430 may comprise an odd number of pulses each having the same pulse width, such as pulses p1 to p5, in which pulses p1, p3, and p5 are of the same polarity and each have an amplitude V, while pulses p2 and p4 are of opposite polarity and each have an amplitude 1.5×V, again providing an asymmetric output that, upon conclusion of the pulse train, provides charge balance.

Figure 12:
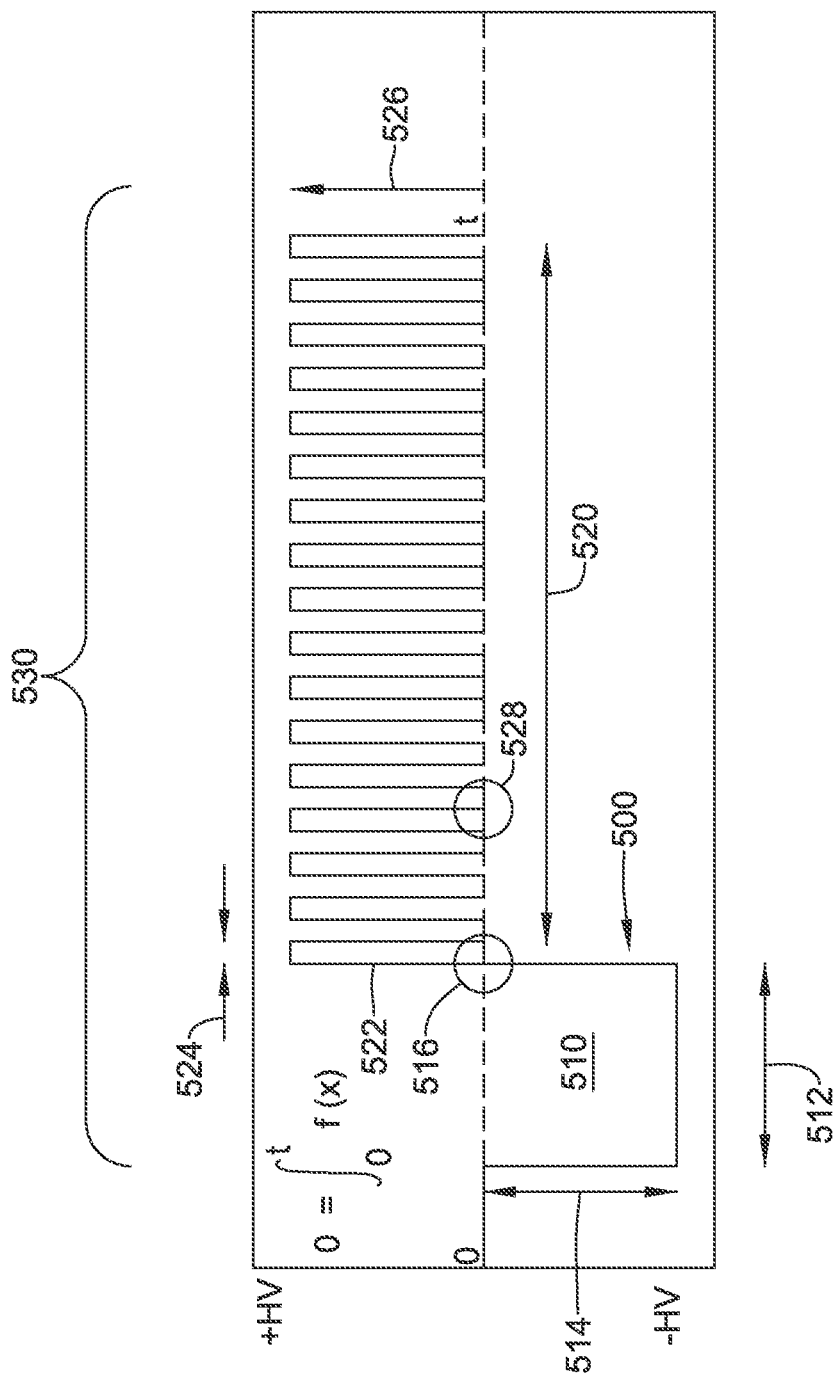

FIG. 12 shows an illustrative therapy waveform. In this example, the method of delivering a multiphasic ablation waveform 500 comprises generating a first pulse 510 of a first polarity having a first amplitude 514 and a first pulse width 512, and generating a first pulse train 520 having a plurality of second pulses 522 of a second polarity opposite the first polarity, the second pulses 522 having second amplitudes 526 and second pulse widths 524, the second pulse widths 524 is a fraction of the first pulse width, such as being less than half, or less than ¼ of the first pulse width 514. The ablation waveform 500 may be delivered such that the first pulse 510 yields a first charge imbalance, and the first pulse train 520 yields a second charge imbalance that offsets the first charge imbalance to prevent muscle stimulation. In this example, the wider pulse width 512 of the first pulse may be relatively long, in fact long enough to start to cause heating of the tissue if delivered repeatedly. However, the offsetting pulse train 520 that follows uses shorter pulse widths and should therefore reduce or even negate the heating effect.

In some further examples, the plurality of second pulses 522 are each separated by an interpulse interval 528, the interpulse interval 528 being between one-half and twice the second pulse width 524. In some examples, the interpulse interval 528 may be even longer than twice the second pulse width 524. For example the interpulse interval may be tens or hundreds of times the pulse widths, such as up to 1000 times the second pulse width. An interphase interval is shown at 516. The interphase interval 516 may be omitted, if desired. If included, an interphase interval may be any suitable length, from a few nanoseconds out to hundreds of microseconds. By spacing the pulse train 520 from the initial pulse 510, a more monophasic result may be achieved. As with other examples, the total period 530 may be selected to be short enough to achieve charge balance without causing muscle stimulation, such as by being shorter than one millisecond.

In some examples, the first pulse width is equal to a sum of the second pulse widths. In still other examples, the first amplitude and the second amplitude each exceed an irreversible electroporation threshold. As noted previously, the relevant IRE threshold may be different depending on the tissue and pulse widths in use.

The example shown indicates that the same amplitude is used for both the first pulse 510 and the pulses 522 of the pulse train 520. In other examples, the first amplitude 514 is less than the second amplitude 526, and the sum of the second pulse widths 524 is less than the first pulse width 512. In some examples, the sum of the second pulse widths 524 and the interpulse intervals 528 (that is, the total duration of the pulsetrain 520) is equal to the first pulse width. The order may be reversed, if desired.

Figure 13:
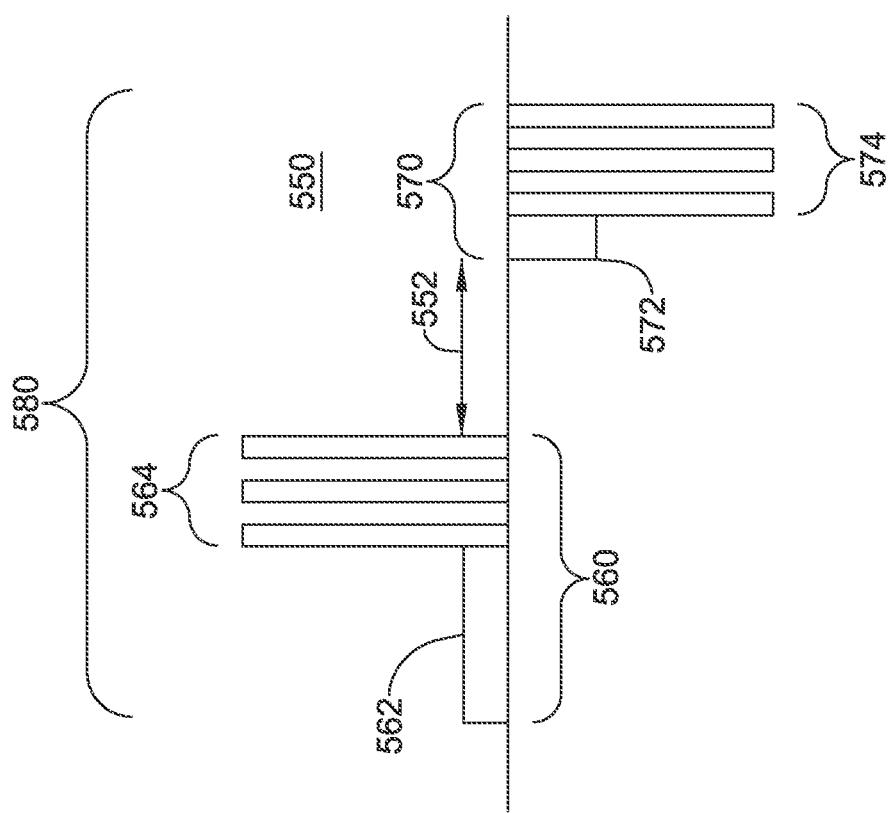

FIG. 13 shows an illustrative therapy waveform. In this example, two complex monopolar outputs are combined to yield a charge balance. A first output 560 comprises a first pulse 562 of relatively lower amplitude, followed by several pulses 564 of higher amplitude and shorter pulse width. The order of 562 and 564 may be reversed, if desired. In another example, the higher amplitude pulses may be superimposed on the first pulse 562.

A second output 570 is delivered some duration of time 552 later. Duration 552 may be any suitable duration but is preferably relatively long, such as being equal to or greater than the duration of the first output 560, while still allowing the total therapy 550 to be delivered in a period 580 of less than one millisecond. The second output 570 may again include a longer pulse width and lower amplitude portion 572 and short pulse width, higher amplitude train 574. In the example, amplitudes for pulse 562 and 572 are different, as are the pulse widths, but that need not be the case and in other pulses 562, 572 are equal in terms of amplitude and pulse width, but of opposite polarity. In an example, the amplitudes for the short pulses 564, 574 are above an IRE threshold (again, in view of the distance between electrodes and the applicable pulse widths), while the other pulses 562, 572 are below the IRE threshold.

In some examples, pulses 562 and 572 are priming pulses that are delivered to prepare the tissue for IRE caused by subsequent pulses. In a further example, the "priming" pulses 562, 572 are of opposite polarity relative to the short pulses 564, 574, respectively.

Figure 14:
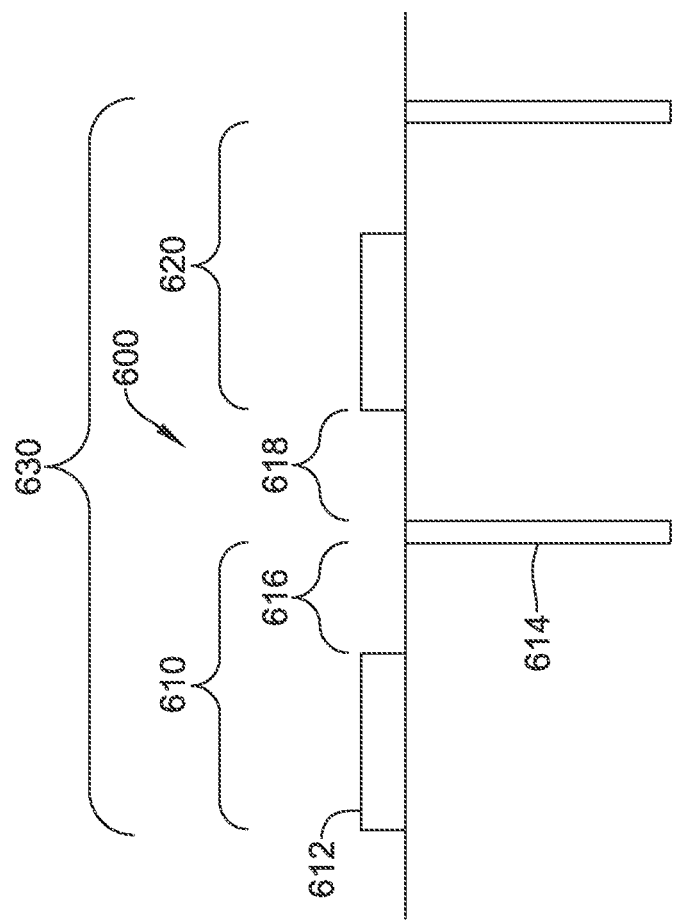

FIG. 14 shows an illustrative therapy waveform. In this example, a first pulse pair 610 is delivered and is itself charge balanced. The first pulse pair 610 includes a first pulse 612 of a first polarity with first pulse width and first amplitude, and a second pulse 614 delivered after an interphase delay 616, the second pulse 614 having an amplitude which is more than twice, and in some examples more than three times the amplitude of the first pulse 612. To achieve charge balancing, the second pulse 614 is much shorter in pulse width than the first pulse 612, wherein a product of the amplitude and pulse width of the first pulse 612 is equal to the product of the amplitude and pulse width of the second pulse 614. A second pulse pair 620 may also be delivered and would be a repeat of the first pulse pair 610, with an interpulse period 618 between the two 610, 620. The time needed to deliver the first pulse pair 610 is preferably less than a time constant of surrounding tissue—that is, pulses 612 and 614 would both be delivered in time to achieve charge balancing without muscle stimulation. The two pulse pairs 610, 620 would be delivered in a physiological window, such as the ST Interval, so that duration 630 is less than the window will allow.

Figure 15:
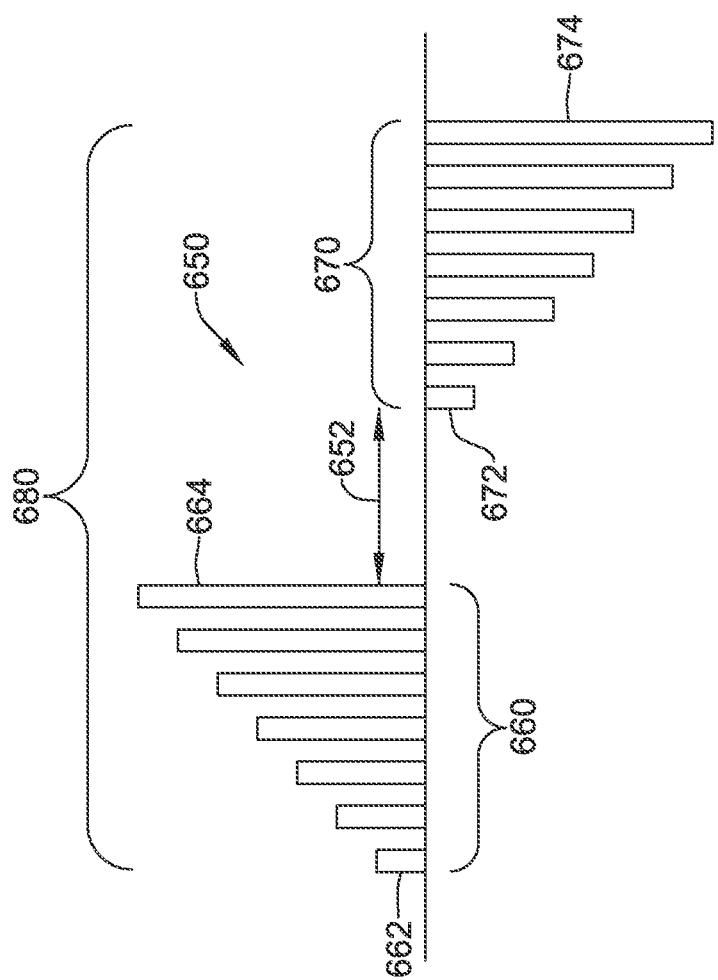

FIG. 15 shows an illustrative therapy waveform 650. This example shows two stepped waveforms 660, 670. More particularly, the figure shows a method of delivering a multiphasic ablation waveform 650 comprising delivering a first pulse train 660 comprising a plurality of first pulses each having a pulse width and an amplitude, wherein a first in time of the first pulses 662 has a first amplitude, and each successive pulse of the first pulses has a larger amplitude than an immediately preceding pulse, each of the first pulses having a first polarity. In some examples, the amplitude of the first pulse 662 in train 660 is less than an IRE threshold, while the last pulse 664 has an amplitude that exceeds the IRE threshold for the tissue, taking into account pulse width and electrode distance. The example method also includes delivering a second pulse train 670 comprising a plurality of second pulses each having a pulse width and an amplitude, wherein a first in time of the second pulses 672 has the first amplitude, and each successive pulse of the second pulses has a larger amplitude than an immediately preceding pulse, each of the second pulses having a second polarity opposite of the first polarity. In some examples, the amplitude of the first pulse 672 in train 670 is less than an IRE threshold, while the last pulse 674 has an amplitude that exceeds the IRE threshold for the tissue, taking into account pulse width and electrode distance. In some examples, the two pulse trains 660 and 670 are equal and opposite, such that, for example, first pulses 662 and 672 each have the same amplitude (but opposite polarity) and pulse width, and the same is true for the last pulses 664, 674. The two pulse trains may be separated by an interval 652 that is at least greater than any of the individual pulse widths, and is preferably at least 4, 8 or 16 times the pulse widths.

In the example, the first pulse train and second pulse train are delivered within a time window 680 of less than about one millisecond, such that charge balance is achieved upon conclusion of the second pulse train 670 without causing muscle stimulation.

In another example, a series of monophasic pulses can be provided which do not add up to a charge balanced pulse train. Within the series of monophasic pulses, some may exceed an IRE threshold, with others exceeding only the reversible electroporation threshold are also applied. A long duty cycle pulse at a lower amplitude can be provided to balance out the series of monophasic pulses, as desired and for charge balancing purposes.

Several embodiments of the present invention take the form of a pulse generator configured for use with a probe for delivering ablation therapy to a patient, the pulse generator comprising output circuitry for delivering voltage-based therapy, monitoring circuitry for monitoring characteristics of delivered therapy pulses, and control circuitry comprising a non-volatile memory containing an executable instruction set adapted to deliver therapy as in any of the above methods.

Several embodiments of the present invention take the form of a system comprising a probe for insertion into a patient having a plurality of electrodes for ablation therapy delivery, and a pulse generator configured for use with the probe for delivering ablation therapy to a patient, the pulse generator comprising output circuitry for delivering voltage-based therapy, monitoring circuitry for monitoring characteristics of delivered therapy pulses, and control circuitry comprising a non-volatile memory containing an executable instruction set adapted to deliver therapy as in any of the above methods.

It should be noted that in the above examples, the terms first, second, third, fourth, etc. when applicable to pulses that are to be delivered do not necessarily indicate an order of delivery of the pulses. A pulse labeled as a "third" pulse may be the first in time to be delivered, relative to pulses labeled as "first," "second," or "fourth", and other orders may be used as well.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, The claimed invention is:

1. A method of delivering a multiphasic ablation waveform comprising:
   generating a first output of a first polarity at a first amplitude for a first time period as a first phase;
   generating a second output of a second polarity, opposite the first polarity, at a second amplitude for a second time period, the second time period being less than half the first time period; and
   generating a third output using the second polarity at a third amplitude less than the second amplitude for a third time period, the third time period being greater than the first time period;
   wherein the sum of the first, second and third outputs yields a balanced charge to limit muscle stimulation associated with the multiphasic ablation waveform; and
   wherein the second output is delivered after the first output, and the third output is delivered after the second output.

2. The method of claim 1 wherein at least one of the first and second amplitudes exceeds an irreversible electroporation threshold, and the third amplitude is less than an irreversible electroporation threshold.

3. The method of claim 1 wherein the first time period is in the range of about 1 to 50 microseconds, and the second time period is in the range of about 0.5 to 10 microseconds.

4. The method of claim 1 wherein the first, second and third outputs are delivered in a sequence having a duration from a start of the first output to an end of the third output which has a duration of less than one millisecond to limit muscle stimulation.

5. A method of treating a patient comprising:
   in a first iteration, each of:
      performing the method of claim 1 to deliver the first, second and third outputs;
      measuring one or more of impedance or current flow for each of the first, second and third outputs; and
      determining that a residual charge imbalance remains after delivery of the first, second and third outputs; and
   in a second iteration, again performing the method of claim 1 and adjusting at least one of the amplitude or pulse width of at least one of the first, second and third outputs to reduce the residual change imbalance;
   wherein the first and second iterations are performed within a time period of less than 10 milliseconds.

6. The method of claim 1, wherein the first and second amplitudes each exceed an irreversible electroporation threshold, and the third amplitude is less than an irreversible electroporation threshold.

7. A method of delivering a multiphasic ablation waveform comprising:
   generating a first pulse of a first polarity having a first amplitude and a first pulse width;
   generating a first pulse train having a plurality of second pulses of a second polarity opposite the first polarity, the second pulses having second amplitudes and second pulse widths, the second pulse widths being less than one-half of the first pulse width;
   such that the first pulse yields a first charge imbalance, and the first pulse train yields a second charge imbalance that offsets the first charge imbalance to prevent muscle stimulation;
   wherein the first pulse width is equal to a sum of the second pulse widths.

8. The method of claim 7 wherein the plurality of second pulses are each separated by an interpulse interval, the interpulse interval being between one-half and twice the second pulse width.

9. The method of claim 7 wherein the first amplitude and the second amplitude each exceed an irreversible electroporation threshold.

10. The method of claim 7, wherein a duration from the start of the first pulse to the end of the first pulse train is less than one millisecond.

* * * * *